US012668571B2

(12) United States Patent
Buhrlage et al.

(10) Patent No.: US 12,668,571 B2
(45) Date of Patent: Jun. 30, 2026

(54) SUBSTITUTED 3-AMINO-4-METHYLBENZENESULFONAMIDES AS SMALL MOLECULE INHIBITORS OF UBIQUITIN-SPECIFIC PROTEASE 28

(71) Applicant: Dana-Farber Cancer Institute, Inc., Boston, MA (US)

(72) Inventors: Sara Buhrlage, Somerville, MA (US); Anthony Varca, Brookline, MA (US); Bin Hu, Natick, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 556 days.

(21) Appl. No.: 18/020,492

(22) PCT Filed: Aug. 10, 2021

(86) PCT No.: PCT/US2021/045317
§ 371 (c)(1),
(2) Date: Feb. 9, 2023

(87) PCT Pub. No.: WO2022/035804
PCT Pub. Date: Feb. 17, 2022

(65) Prior Publication Data

US 2023/0271918 A1 Aug. 31, 2023

Related U.S. Application Data

(60) Provisional application No. 63/063,667, filed on Aug. 10, 2020.

(51) Int. Cl.

| | |
|---|---|
| ***C07C 233/65*** | (2006.01) |
| ***C07C 311/46*** | (2006.01) |
| ***C07C 317/40*** | (2006.01) |
| ***C07D 233/61*** | (2006.01) |
| ***C07D 295/108*** | (2006.01) |
| ***C07D 295/135*** | (2006.01) |
| ***C07D 295/26*** | (2006.01) |

(52) U.S. Cl.
CPC .......... *C07C 311/46* (2013.01); *C07C 233/65* (2013.01); *C07C 317/40* (2013.01); *C07D 233/61* (2013.01); *C07D 295/108* (2013.01); *C07D 295/135* (2013.01); *C07D 295/26* (2013.01)

(58) Field of Classification Search
CPC ............................ C07C 233/65; C07C 311/46
See application file for complete search history.

(56) References Cited

U.S. PATENT DOCUMENTS

| | | | |
|---|---|---|---|
| 1,909,960 | A | 5/1933 | Hitch |
| 9,067,894 | B1 | 6/2015 | Weaver |

FOREIGN PATENT DOCUMENTS

| | | | |
|---|---|---|---|
| EP | 0 887 341 | A1 | 12/1998 |
| WO | WO-2008/147962 | A1 | 12/2008 |
| WO | WO-2010/043592 | A1 | 4/2010 |
| WO | WO-2019/145726 | A1 | 8/2019 |
| WO | WO-2022/035804 | A1 | 2/2022 |

OTHER PUBLICATIONS

Registry No. 1095326-89-8, retrieved from Registry; entered in STN on Jan. 23, 2009; Supplier: UkOrgSynthesis.*
Registry No. 1095326-84-3, retrieved from Registry; entered in STN on Jan. 23, 2009; Supplier: UkOrgSynthesis.*
Registry No. 1095326-78-5, retrieved from Registry; entered in STN on Jan. 23, 2009; Supplier: UkOrgSynthesis.*
Registry No. 1001574-75-9, retrieved from Registry; entered in STN on Feb. 5, 2008; Database: Zinc.*
Registry No. 949728-03-4, retrieved from Registry; entered in STN on Oct. 9, 2007; Supplier: Enamine.*
Registry No. 871664-65-2, retrieved from Registry; entered in STN on Jan. 11, 2006; Supplier: Enamine.*
Registry No. 698974-66-2, retrieved from Registry; entered in STN on Jun. 25, 2004; Supplier: Maybridge plc.*
No new references cited by the Examiner.*
International Preliminary Report on Patentability for International Application No. PCT/US2021/045317 dated Feb. 23, 2023.
International Search Report and Written Opinion for International Application No. PCT/US2021/045317 dated Nov. 10, 2021.
Liu et al., "Design, synthesis and in vitro activities on anti-platelet aggregation of 4-methoxybenzene-1,3-isophthalamides," Bioorganic & Medicinal Chemistry Letters, 22(21): 6591-6595 (2012).
Milite et al., "Novel 2-substituted-benzimidazole-6-sulfonamides as carbonic anhydrase inhibitors: synthesis, biological evaluation against isoforms I, II, IX and XII and molecular docking studies," Journal of Enzyme Inhibition and Medicinal Chemistry, 34(1): 1697-1710 (2019).
Sippl et al., "Ubiquitin-specific proteases as cancer drug targets," Future Oncology, 7(5): 619-632 (2001).

(Continued)

*Primary Examiner* — Shawquia Jackson
(74) *Attorney, Agent, or Firm* — Foley Hoag LLP; DeAnn F. Smith; Laura A. Wzorek

(57) ABSTRACT

The present disclosure relates to a compound of formula (I) or a pharmaceutically acceptable salt thereof and pharmaceutical composition comprising the compound of formula (I). The present composition also relates to methods treating a disease or disorder associated with ubiquitin-specific protease 28 (USP28), methods of treating cancer, and methods of inhibiting USP28.

(I)

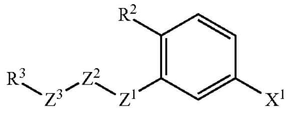

21 Claims, 4 Drawing Sheets

(56) References Cited

OTHER PUBLICATIONS

Wrigley et al., "Identification and Characterization of Dual Inhibitors of the USP25/28 Deubiquitinating Enzyme Subfamily," ACS Chem Biol, 12(12): 3113-3125 (2017).
Yang et al., "Viral Infectivity Factor: A Novel Therapeutic Strategy to Block HIV-1 Replication," Mini-Reviews in Medicinal Chemistry, 13(7): 1047-1055 (2013).

* cited by examiner

SUBSTITUTED 3-AMINO-4-METHYLBENZENESULFONAMIDES AS SMALL MOLECULE INHIBITORS OF UBIQUITIN-SPECIFIC PROTEASE 28

CROSS-REFERENCE TO RELATED APPLICATIONS

This application is a U.S. National Phase of International Patent Application No. PCT/US21/45317, filed Aug. 10, 2021, which claims the benefit of priority to U.S. Provisional Patent Application No. 63/063,667, filed on Aug. 10, 2020, the contents of each of which are hereby incorporated herein by reference in their entirety.

BACKGROUND

Ubiquitin is a small protein consisting of 76 amino acids that is important in the regulation of protein function in the cell. Ubiquitination and deubiquitination are enzymatically mediated processes by which ubiquitin is covalently bound to or unbound from a target protein. These processes have been implicated in the regulation of the cell cycle, apoptosis, the marking of transmembrane proteins such as receptors for removal, regulation of DNA transcription and repair, and other important functions. Proteins are targeted for degradation by the proteasome in the cell by being "tagged" with three or more ubiquitin molecules (polyubiquitination). The binding of a single ubiquitin molecule (monoubiquitination) does not generally target the monoubiquitinated protein for degradation. Rather, it may trigger activities such as DNA repair and gene silencing, among other functions.

Research into the post-translation modification (PTM) of ubiquitination and its role in biology and therapeutic relevance has been increasingly studied since the discovery of the ubiquitin-proteasome system 20 years ago. Currently, it is one of the most intensely investigated PTMs with interest driven by the appeal of developing therapeutics that modulate ubiquitination to promote selective degradation of proteins relevant in disease. Perhaps the highest profile demonstration of this promise is the retrospective discovery of the mechanism of action of thalidomide and related compounds, which are referred to as imides. These agents are approved for the treatment of multiple myeloma and other hematological malignancies. These imides function as molecular glues that recruit different proteins, such as transcription factors IKZF1 and IKZF3, to the DDB1-CRBN E3 ubiquitin ligase complex. This results in their ubiquitination and degradation by the proteasome. Preclinical studies provide further evidence that high-precision protein degradation can be achieved by small molecule agents that either recruit an E3 ligase to the target of interest, or inhibit the deubiquitinating enzyme acting to remove ubiquitin from the protein.

Deubiquitination allows ubiquitin to be recycled and restores the function of the deubiquitinated proteins. Ubiquitin molecules are cleaved from a protein by deubiquitinating enzymes (DUBs). Despite growing interest in their function and potential as therapeutic targets, there are few selective small molecule probes for DUBs and no approved DUB-targeting drugs.

There are currently around 100 reported mammalian DUBs divided broadly into two classes based on their catalytic mechanism (cysteine proteases and zinc metalloproteases). The large number (~90) of cysteine protease DUBs are further subdivided into six families based on sequence homology. DUBs have been found to regulate a myriad of physiological processes including protein degradation, DNA repair, protein trafficking, innate immunity, and signaling pathways. They are implicated in numerous diseases including cancer, neurodegeneration, and inflammation/immune response.

Given the accumulating evidence that DUBs represent promising therapeutic targets and recent studies demonstrating that the enzyme family is tractable for probe and drug development, there is increased interest in high quality chemical probes to investigate fundamental questions surrounding DUB function as well as their promise and liabilities as drug targets. High throughput diversity library screening is frequently employed for first-in-class inhibitor development and has been featured prominently in discovery of DUB inhibitors. However, these studies have had limited success in yielding drug-like compounds with good selectivity. Substrate or ligand-based design strategies have been successful in hit and lead identification for other protein families including caspases, kinases, and methyl lysine reader proteins. In the case of DUBs, it has been shown that full-length ubiquitin can serve as a template for development of protein-based inhibitors, but efforts to identify short peptides that could serve starting points for small molecule inhibitor development have been unsuccessful. Previous DUB HTS campaigns have focused on a single DUB of interest. It was hypothesized that executing a high throughput screening campaign with a target class approach in mind, namely upfront interrogation of selectivity through parallel DUB screening, had the potential to be more successful than previous single DUB screens.

Ubiquitin-specific protease 28 (USP28) is a cysteine isopeptidase of the USP sub-family of DUBs. USP28 exerts its function through regulating the stability of a plethora of cellular proteins. USP28 has been characterized as a tumor-promoting factor and has been found to stabilize many oncoproteins.

Amplification, deletions and mutations of USP28 have been identified in multiple cancer types, including breast cancer, acute myeloid leukemia (AML), ovarian cancer, and colorectal cancer. Furthermore, USP28 overexpression has been correlated with poor prognosis in patients with glioblastoma, non-small cell lung carcinoma and bladder cancers suggesting that USP28 plays an important role in tumorigenesis of these tumor types.

USP28 is also known to play a role in the control of the stability of MYC protein. MYC is a master regulator of the transcription of genes involved in cell growth, proliferation and apoptosis and is essential for tumor initiation and maintenance in many tumor types. In addition, MYC is the most frequently amplified oncogene in human cancer, with alterations in many tumor types including breast, lung and prostate. Knockdown of the USP28 gene has been shown to lead to a decrease of MYC protein and an associated inhibition of growth in a panel of human cancer cell lines in vitro.

USP28 has also been reported to be required to impart stability on the LSD1 (lysine-specific demethylase 1) protein. LSD1 is a histone demethylase that complexes with many partner proteins to control cellular pluripotency and differentiation. Knockdown of USP28 in tumor cells has been shown to lead to the destabilization of LSD1 protein, the suppression of cancer stem cell (CSC)-like characteristics in vitro, and the inhibition of tumor growth in vivo. Small molecule inhibitors of LSD1 have shown antitumor activity in models of AML and Ewing sarcoma. Thus, USP28 inhibition represents an alternate approach to targeting LSD1 in these tumor types.

USP28 inhibition has also been shown to reduce NICD1-levels and to lead to inhibition of the NOTCH pathway activity. NOTCH signaling controls diverse cellular differentiation decisions and drives tumorigenesis in certain tumor types. NOTCH1 is a potent T-cell oncogene, with >50% of T-cell acute lymphoblastic leukemia (T-ALL) cases carrying activating mutations in NOTCH1. NOTCH1 rearrangements lead to constitutive pathway activation and drive tumorigenesis in many cancer types, including triple-negative breast cancer.

Other reported substrates of USP28 include c-Jun, Cyclin E, HIF-1α, Claspin, 53BP1, and Mdc1, many of which play important roles in tumorigenesis in humans. Many USP28 substrates are recognized by FBW7, the substrate recognition subunit of SCF (FBW7) E3 ubiquitin ligase. FBW7 recognizes USP28 substrates in a phosphorylation-dependent manner and targets them for ubiquitination ultimately leading to their proteasomal degradation. The antagonizing roles of USP28 and FBW7 on their shared oncoprotein substrates indicate the intricate nature of protein stability control and may provide additional therapeutic opportunities for cancer treatment.

Mice with a germline knockout of USP28 have been shown to be viable and fertile, confirming that USP28 activity is not required for normal development and reproductive function. Conditional knockout of USP28 in mouse intestine led to the reduction of oncoproteins including c-Myc, active NOTCH (NICD1) and c-JUN which was associated with decreased intestinal cell proliferation and enhanced differentiation. More importantly, intestinal tumorigenesis induced by APC mutation was effectively blocked with acute USP28 depletion suggesting that USP28 could be an appealing target to reduce tumor burden and improve survival for intestinal cancers.

In summary, USP28 plays an important role in promoting tumorigenesis in cells and modulating immune responses. Its major role is in the deubiquitination and stabilization of diverse oncoproteins and epigenetic drivers and immunomodulatory proteins among other cellular factors, which are necessary for immune responses and tumor initiation and growth in humans. Inhibition of USP28 with small molecule inhibitors therefore has the potential to be a treatment for cancers, autoimmune diseases, inflammatory diseases, infectious diseases, and other disorders. For this reason, there remains a considerable need for novel and potent small molecule inhibitors of USP28.

SUMMARY

In some aspects, the present disclosure relates to a compound of formula (I)

(I)

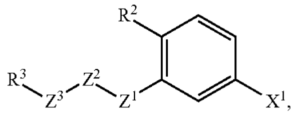

or a pharmaceutically acceptable salt thereof, wherein, independently for each occurrence, $X^1$ is —C(═O)$NR^8$($C_{1-3}$ alkyl) or —$S(O)_2R^1$;

$R^1$ is $C_{1-2}$ alkyl or —$NR^4R^5$;

$R^4$ is H or $C_{1-3}$ alkyl;

$R^5$ is $C_{1-3}$ alkyl or $C_{6-10}$ aryl, or $R^4$ and $R^5$, together with the nitrogen atom to which they are attached, optionally form a $C_{5-8}$ heterocyclyl;

$R^2$ is H, $C_{1-3}$ alkyl, —$OR^6$, or Hal;

$R^6$ is H, $C_{1-3}$ alkyl, or —$C(Hal)_3$;

$Z^1$ is —C(═O)— or —$NR^8$—;

$R^8$ is H or $C_{1-3}$ alkyl;

$Z^2$ is —C(═O)— or —$NR^B$—, or $R^2$, $Z^2$, and $Z^1$, taken together with the atoms to which they are attached, form a $C_{5-6}$ heteroaryl, $Z^3$ is absent or $C_{1-3}$ alkylene; and $R^3$ is $C_{6-10}$ aryl, $C_{5-6}$ heteroaryl, or $C_{5-8}$ heterocyclyl; and wherein each $C_{1-3}$ alkyl, $C_{6-10}$ aryl, $C_{5-6}$ heteroaryl, and $C_{5-8}$ heterocyclyl is independently optionally substituted with one or more groups selected from $C_{1-3}$ alkyl, $C_{6-10}$ aryl, $C_{5-8}$ heterocyclyl, Hal, —$C(Hal)_3$, —OH, —$NO_2$, —NHC(═O)($C_{1-3}$ alkyl), and —NH($C_{1-3}$ alkyl), or a combination thereof.

In some embodiments, the compound is not

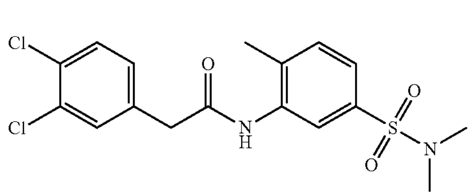

or

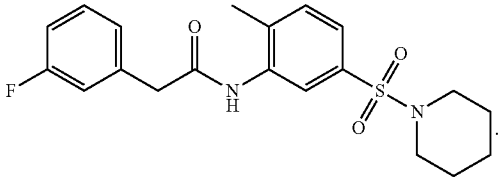

In some aspects, the present disclosure relates to a method of treating a disease or disorder associated with ubiquitin-specific protease 28 (USP28), comprising administering to a subject in need thereof a compound of formula (I) or formula (II), a compound selected from compounds 1-27 and 29-31, or a pharmaceutical composition of the disclosure.

In some aspects, the present disclosure relates to a method of treating cancer, comprising administering to a subject in need thereof a compound of formula (I) or formula (II), a compound selected from compounds 1-27 and 29-31, or a pharmaceutical composition of the disclosure.

In some aspects, the present disclosure relates to a method of inhibiting USP28 in a subject in need thereof, comprising administering to the subject a compound of formula (I) or formula (II), a compound selected from compounds 1-27 and 29-31, or a pharmaceutical composition of the disclosure.

In some aspects, the present disclosure relates to a use of a compound of formula (I) or formula (II), a compound selected from compounds 1-27 and 29-31, for the manufacture of a medicament for treating a disease or disorder associated with USP28.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

Overview

Figure 1:
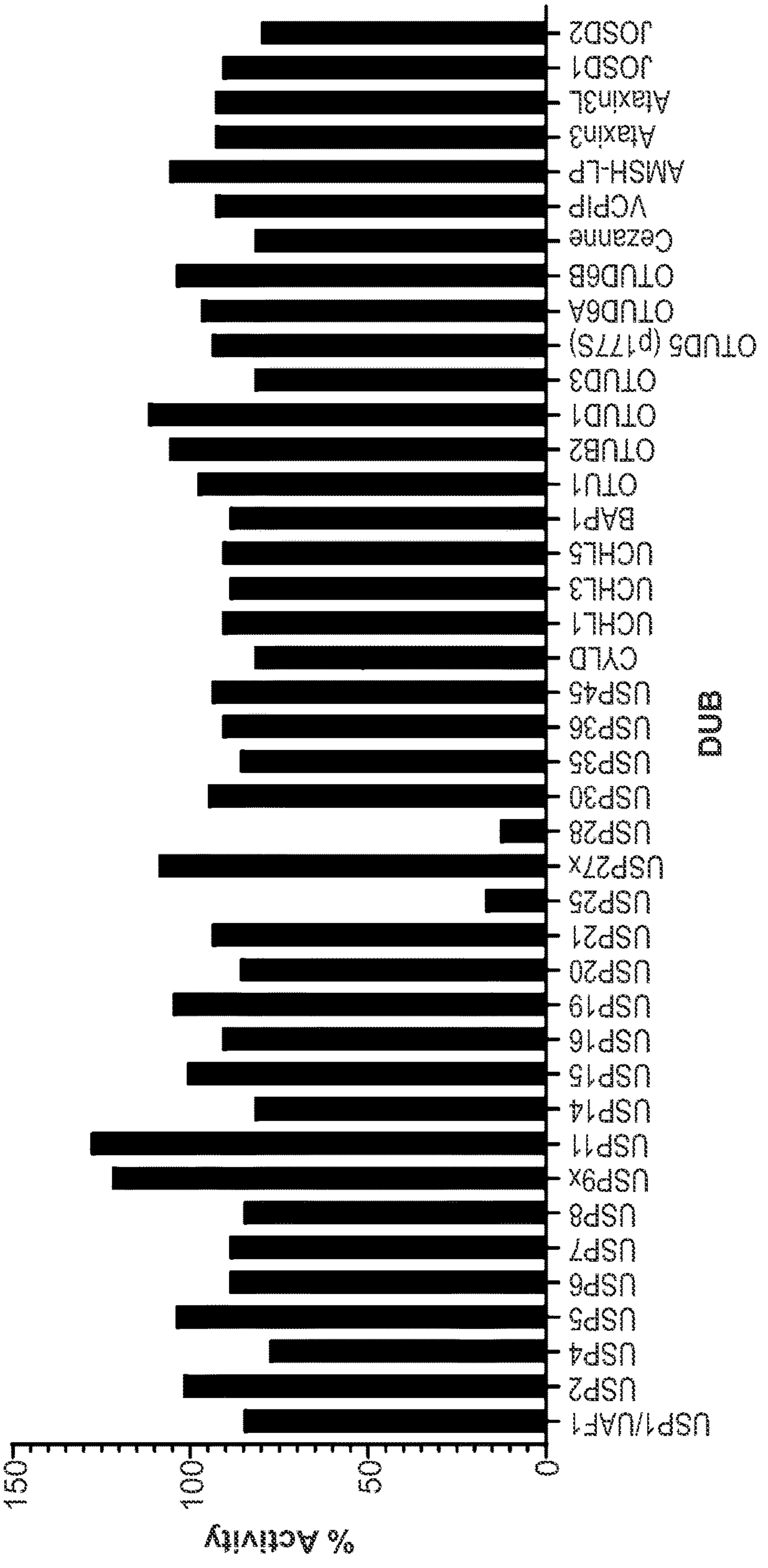
FIG. 1 depicts Ubiquigent profiling data plot for compound 1. Compound 1 was tested at 100 μM against a panel of 41 purified Deubiquitinase enzymes (DUBs), % activity of DUBs with compound treatment reported.

A description of example embodiments of the invention follows.

In some embodiments, the present disclosure relates to a compound of formula (I)

(I)

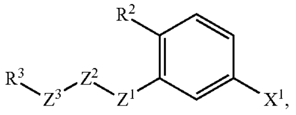

or a pharmaceutically acceptable salt thereof, wherein, independently for each occurrence, $X^1$ is —C(═O)$NR^8$($C_{1-3}$ alkyl) or —$S(O)_2R^1$;

$R^1$ is $C_{1-2}$ alkyl or —$NR^4R^5$;

$R^4$ is H or $C_{1-3}$ alkyl;

$R^5$ is $C_{1-3}$ alkyl or $C_{6-10}$ aryl, or $R^4$ and $R^5$, together with the nitrogen atom to which they are attached, optionally form a $C_{5-8}$ heterocyclyl;

$R^2$ is H, $C_{1-3}$ alkyl, —$OR^6$, or Hal;

$R^6$ is H, $C_{1-3}$ alkyl, or —C(Hal)$_3$;

$Z^1$ is —C(═O)— or —$NR^8$—;

$R^8$ is H or $C_{1-3}$ alkyl;

$Z^2$ is —C(═O)— or —$NR^8$—, or $R^2$, $Z^2$, and $Z^1$, taken together with the atoms to which they are attached, form a $C_{5-6}$ heteroaryl, $Z^3$ is absent or $C_{1-3}$ alkylene; and $R^3$ is $C_{6-10}$ aryl, $C_{5-6}$ heteroaryl, or $C_{5-8}$ heterocyclyl; and wherein each $C_{1-3}$ alkyl, $C_{6-10}$ aryl, $C_{5-6}$ heteroaryl, and $C_{5-8}$ heterocyclyl is independently optionally substituted with one or more groups selected from $C_{1-3}$ alkyl, $C_{6-10}$ aryl, $C_{5-8}$ heterocyclyl, Hal, —C(Hal)$_3$, —OH, —$NO_2$, —NHC(═O)($C_{1-3}$ alkyl), and —NH($C_{1-3}$ alkyl), or a combination thereof.

In some embodiments, the compound is not

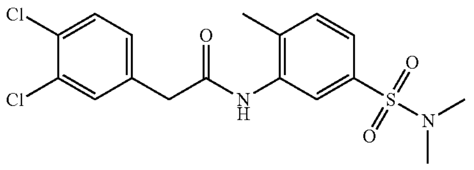

or

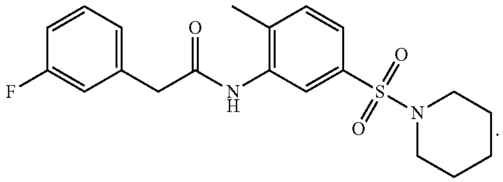

In some embodiments, $X^1$ is —C(═O)$NR^8$($C_{1-3}$ alkyl), wherein $C_{1-3}$ alkyl is optionally substituted with one or more $C_{6-10}$ aryls. In some embodiments, $X^1$ is —$S(O)_2R^1$.

In some embodiments, $Z^1$ is —$NR^8$—. In some embodiments, $R^2$, $Z^2$, and $Z^1$, taken together with the atoms to which they are attached, form a $C_{5-6}$ heteroaryl.

In some embodiments, the compound a compound of formula (II)

(II)

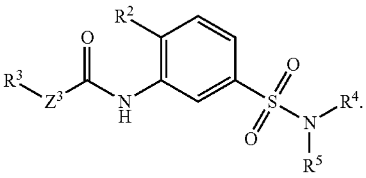

In some embodiments, $R^4$ is H. In some embodiments, $R^4$ is $C_{1-3}$ alkyl. In some embodiments, $R^4$ is methyl.

In some embodiments, $R^5$ is $C_{1-3}$ alkyl. In some embodiments, $R^5$ is methyl. In some embodiments, $R^4$ and $R^5$, together with the nitrogen atom to which they are attached, form a $C_{5-8}$ heterocyclyl. In some embodiments, $R^5$ is $C_{1-3}$ alkyl substituted with one or more $C_{6-10}$ aryls. In some embodiments, $R^5$ is benzyl. In some embodiments, $R^5$ is $C_{6-10}$ aryl. In some embodiments, $R^5$ is phenyl. In some embodiments, $R^4$ is methyl and $R^5$ is methyl. In some embodiments, $R^4$ is H and $R^5$ is benzyl.

In some embodiments, $R^2$ is H. In some embodiments, $R^2$ is $C_{1-3}$ alkyl. In some embodiments, $R^2$ is methyl. In some embodiments, $R^2$ is ethyl. In some embodiments, $R^2$ is benzyl. In some embodiments, $R^2$ is Hal. In some embodiments, $R^2$ is Cl.

In some embodiments, $Z^3$ is $C_{1-2}$ alkylene. In some embodiments, $Z^3$ is $C_1$ alkylene. In some embodiments, $Z^3$ is $C_2$ alkylene.

In some embodiments, $R^3$ is $C_{6-10}$ aryl. In some embodiments, $R^3$ is phenyl. In some embodiments, $R^3$ is unsubstituted. In some embodiments, $R^3$ is substituted with one or more groups selected from $C_{1-3}$ alkyl, $C_{6-10}$ aryl, $C_{5-8}$ heterocyclyl, —OH, Hal, —C(Hal)$_3$, —$NO_2$, —NHC(═O)

($C_{1-3}$ alkyl), and —NH($C_{1-3}$ alkyl), or a combination thereof. In some embodiments, $R^3$ is substituted with one or more Hal. In some embodiments, $R^3$ is substituted with one or more —OH. In some embodiments, $R^3$ is substituted with one or more —$NO_2$. In some embodiments, $R^3$ is substituted with one or more $C_{6-10}$ aryl. In some embodiments, $R^3$ is

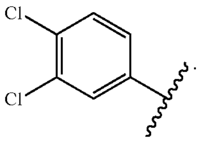 [SMILES: *c1ccc(Cl)c(Cl)c1]

In some embodiments, the present disclosure relates to a compound selected from

1

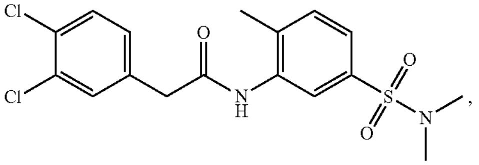

2

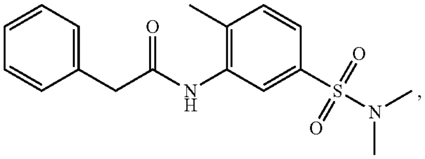

3

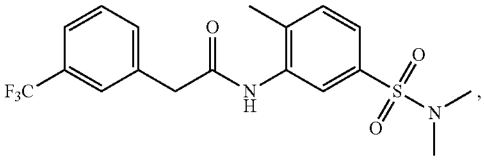

4

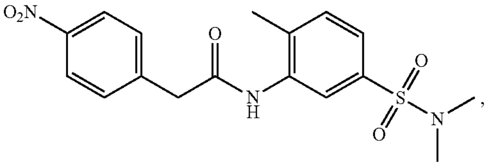

5

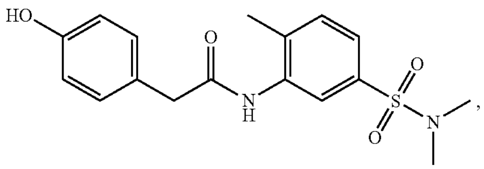

6

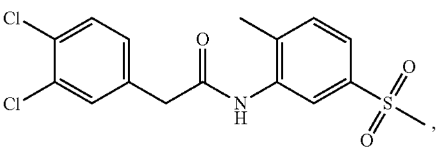

7

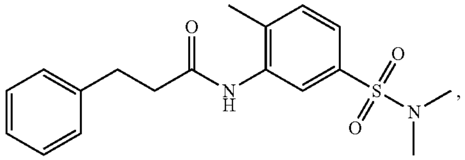

-continued

8

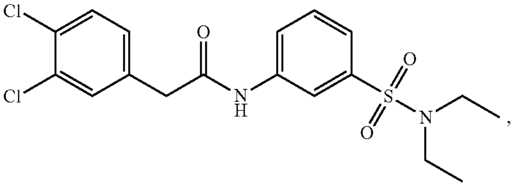

9

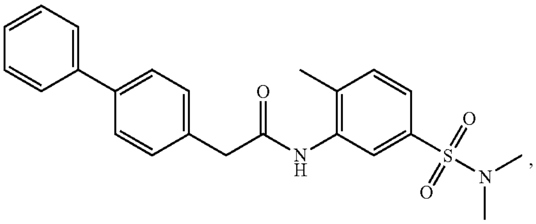

10

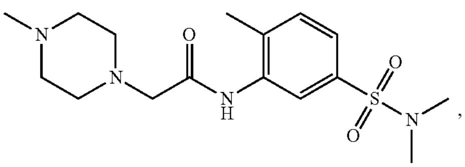

11

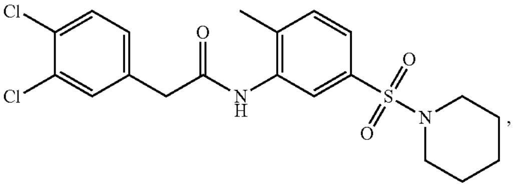

12

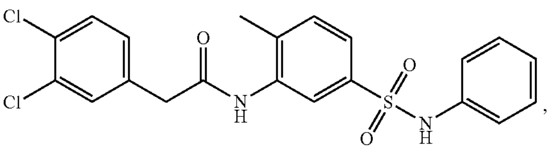

13

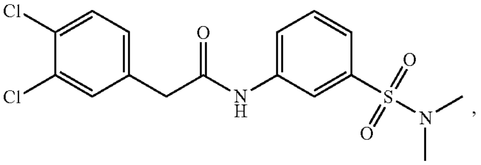

14

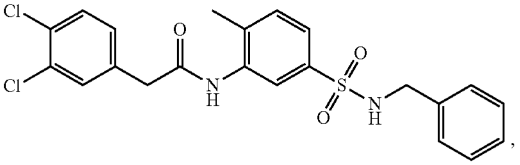

15

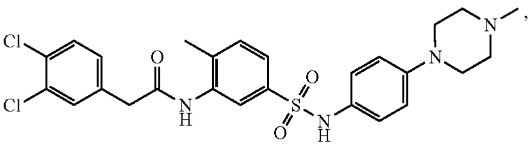

-continued
16
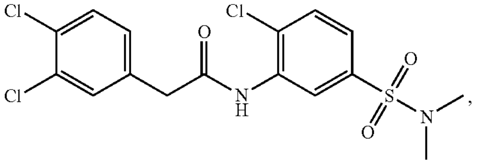
17
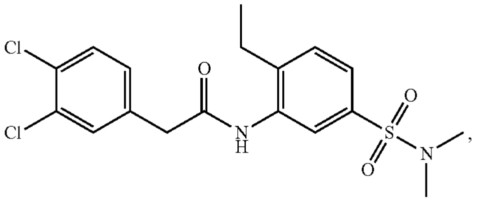
18
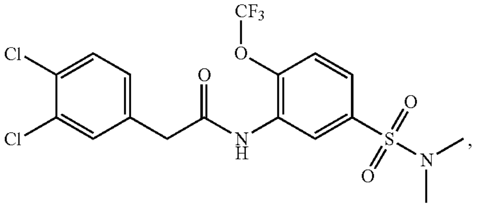
19
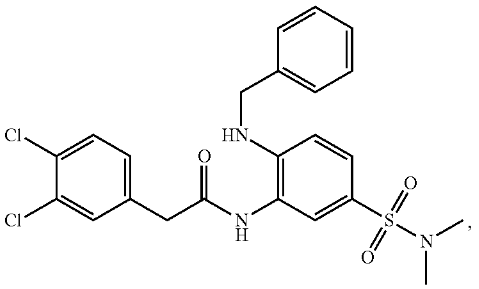
20
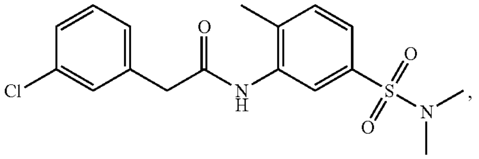
21
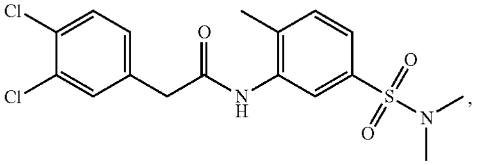
22
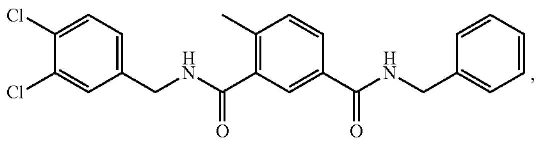
23
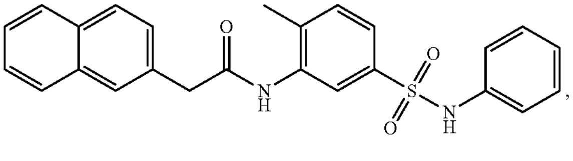
-continued
24
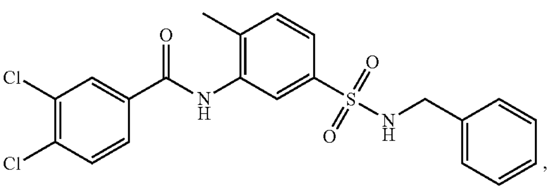
25
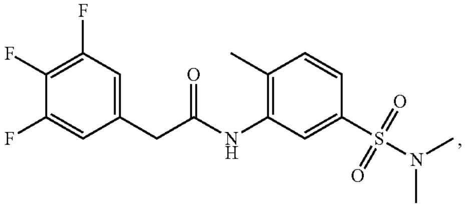
26
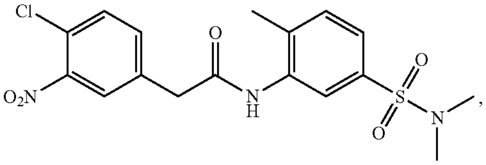
27
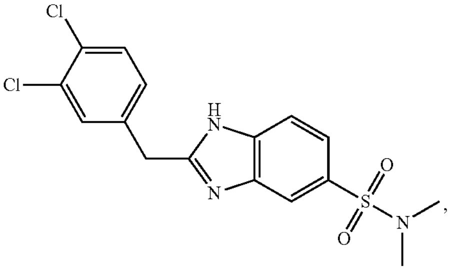
29
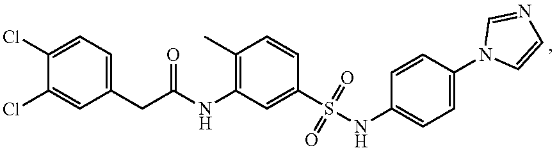
30
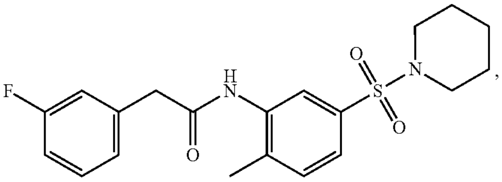
and
31
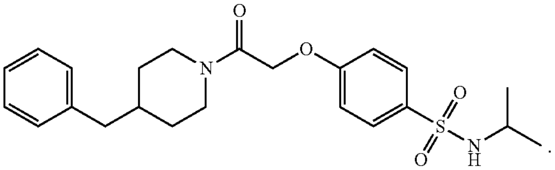
In some embodiments, the compound is selected from compounds 2-27 and 29. In certain embodiments, the disclosure relates to a compound selected from compounds 2, 3, 5, 7, 8, 10-12, 14-17, 20-24, and 29. In preferred embodiments, the disclosure relates to a compound selected from compounds 11, 12, 14-16, 20, 21, 23, and 24.

In certain embodiments, the compound is not compound 1, 30, or 31.

In some aspects, the present disclosure relates to a pharmaceutical composition comprising a compound of formula (I) or formula (II), such as a compound selected from compounds 2-27 and 29, and a pharmaceutically acceptable carrier.

In some aspects, the present disclosure relates to a method of treating a disease or disorder associated with ubiquitin-specific protease 28 (USP28), comprising administering to a subject in need thereof a compound of formula (I), a compound of formula (II), a compound selected from compounds 1-31, or a pharmaceutical composition of the disclosure. According to these aspects, any of the embodiments of formula (I) or formula (II) may be used, in particular the embodiments described above with respect to formula (I) or formula (II). In some embodiments, the disease or disorder associated with USP28 is cancer. In some aspects, the present disclosure relates to a method of treating cancer, comprising administering to a subject in need thereof a compound of formula (I) or formula (II), a compound selected from compounds 1-27 and 29-31, or a pharmaceutical composition of the disclosure.

In some embodiments, the cancer is liposarcoma, neuroblastoma, glioblastoma, breast cancer, bladder cancer, glioma, adrenocortical cancer, multiple myeloma, acute myeloid leukemia, T-cell acute lymphoblastic leukemia, colorectal cancer, colon cancer, prostate cancer, non-small cell lung cancer, Human Papilloma Virus-associated cervical cancer, oropharyngeal cancer, penis cancer, ovarian cancer, anal cancer, thyroid cancer, vaginal cancer, Epstein-Barr Virus-associated nasopharyngeal carcinoma, gastric cancer, rectal cancer, thyroid cancer, Hodgkin lymphoma, diffuse large B-cell lymphoma, or Ewing sarcoma. In some embodiments, the cancer is neuroblastoma, multiple myeloma, acute myeloid leukemia, breast cancer, glioma, colon cancer, prostate cancer, or ovarian cancer. In some embodiments, the cancer is multiple myeloma. In some embodiments, the cancer is Ewing sarcoma. In some embodiments, the cancer is acute myeloid leukemia.

In some aspects, the present disclosure relates to a method of inhibiting USP28 in a subject in need thereof, comprising administering to the subject a compound of formula (I) or formula (II), a compound selected from compounds 1-27 and 29-31, or a pharmaceutical composition of the disclosure.

In some aspects, the present disclosure relates to a use of a compound of formula (I) or formula (II), or a compound selected from compounds 1-27 and 29-31, for the manufacture of a medicament for treating a disease or disorder associated with USP28.

Pharmaceutical Compositions

The compositions and methods of embodiments of the invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

In some embodiments, the disclosure includes the use of pharmaceutically acceptable salts of compounds of the invention in the compositions and methods of the invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d glucoheptonic acid, d gluconic acid, d glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, l-pyroglutamic acid, salicylic acid, sebacic acid, stearic acid, succinic acid, sulfuric acid, 1 tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques described herein are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds described herein can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

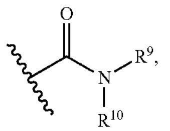

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

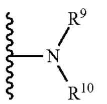

or

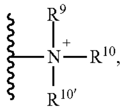

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

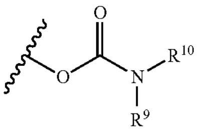

or

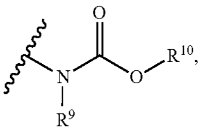

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" ("hal") as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group $-OSO_3H$, or a pharmaceutically acceptable salt thereof.

The term "sulfonamide" is art-recognized and refers to the group represented by the general formulae

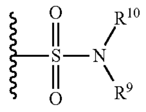
or
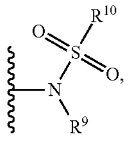

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group $SO_3H$, or a pharmaceutically acceptable salt thereof.

The term "sulfone" is art-recognized and refers to the group $-S(O)_2-$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $-C(O)SR^9$ or $-SC(O)R^9$, wherein $R^9$ represents a hydrocarbyl.

The term "thioether", as used herein, is equivalent to an ether, wherein the oxygen is replaced with a sulfur.

The term "urea" is art-recognized and may be represented by the general formula

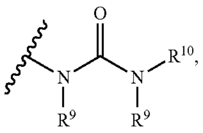

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form a compound described herein (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. In certain embodiments, the disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

Exemplary Methods

In another embodiment, the present invention relates to a method of treating or lessening the severity of a disease or condition selected from a proliferative disorder (e.g., cancer), wherein said method comprises administering to a patient in need thereof a compound or composition according to the present invention. In a more specific embodiment, the present invention relates to a method of treating or lessening the severity of cancer. Specific examples of the above disorders are set forth in detail below.

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer (e.g., esophageal squamous cell cancer); Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood;

Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor.

Further exemplary cancers include diffuse large B-cell lymphoma (DLBCL) and mantle cell lymphoma (MCL). Yet further exemplary cancers include endocervical cancer, B-cell ALL, T-cell ALL, B- or T-cell lymphoma, mast cell cancer, glioblastoma, neuroblastoma, follicular lymphoma and Richter's syndrome.

Exemplary sarcomas include fibrosarcoma, alveolar soft part sarcoma (ASPS), liposarcoma, leiomyosarcoma, chondrosarcoma, synovial sarcoma, chordoma, spindle cell sarcoma, histiocytoma, rhabdomyosarcoma, Ewing's sarcoma, neuroectodermal sarcoma, phyllodes/osteogenic sarcoma and chondroblastic osteosarcoma.

Metastases of the aforementioned cancers can also be treated or prevented in accordance with the methods described herein.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

Cancer Combination Therapies

In some embodiments, a compound described herein is administered together with an additional cancer treatment. Exemplary additional cancer treatments include, for example: chemotherapy, targeted therapies such as antibody therapies, kinase inhibitors, immunotherapy, and hormonal therapy, epigenetic therapy, proteosome inhibitors (e.g., carfilzomib), and anti-angiogenic therapies. Examples of each of these treatments are provided below. As used herein, the term "combination," "combined," and related terms refer to the simultaneous or sequential administration of therapeutic agents in accordance with this invention. For example, a compound of the present invention can be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustin, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Hormonal therapy agents include the administration of hormone agonists or hormone antagonists and include retinoids/retinoic acid, compounds that inhibit estrogen or testosterone, as well as administration of progestogens.

EXAMPLES

Abbreviations used in the following examples and elsewhere herein are:

atm atmosphere
BCA bicinchoninic acid
BME beta-mercaptoethanol
DCM dichloromethane
DEA diethylamine
DIPEA N,N-diisopropylethylamine
DMA N,N-dimethylacetamide
DMF N,N-dimethylformamide
DMSO dimethyl sulfoxide
DTT dithiothreitol
EA ethyl acetate
EDTA ethylenediaminetetraacetic acid
ESI electrospray ionization
$Et_2O$ diethyl ether
h hour(s)
HATU [bis(dimethylamino)methylene]-1H-1,2,3-triazolo [4,5-b]pyridinium 3-oxide
hexafluorophosphate
Hex hexane
HEPES 4-(2-hydroxyethyl)-1-piperazineethanesulfonic acid
HPLC high-performance liquid chromatography
ITC isothermal titration calorimetry
LCMS liquid chromatography-mass spectrometry
LDS lithium dodecyl sulfate
min minutes
NMR nuclear magnetic resonance
NP-40 nonyl phenoxypolyethoxylethanol
PMSF phenylmethylsulfonyl fluoride
ppm parts per million
r.t. room temperature
SDS-PAGE sodium dodecyl sulfate-polyacrylamide gel electrophoresis
SP3 single-pot solid-phase-enhanced sample preparation
TCEP tris(2-carboxyethyl)phosphine
TEA triethylamine
TEAB triethylammonium bicarbonate
TFA trifluoroacetic acid
THE tetrahydrofuran
TLC thin layer chromatography
TMT tandem mass tag
UPLC ultra performance liquid chromatography

Biological Assays

Example 1. Ubiquitin-Rhodamine110 Assay

USP28 (at 1 nM) was pre-incubated with different concentrations of inhibitors or DMSO as a control in 50 mM Tris pH 8, 50 mM NaCl, 0.002% Tween-20, 5 mM DTT. Compounds and protein were incubated for 30 minutes at room temperature prior to the addition of Ubiquitin-Rho110 (Boston Biochem) substrate for a final concentration of 125 nM. The initial rate of the reaction was measured by collecting fluorescence data at one-minute interval over 30-minute period using a Clariostar® fluorescence plate reader at excitation and emission wavelength of 485 nm and 535 nm, respectively. The calculated initial rate values were plotted against inhibitor concentrations to determine IC50s. All the experimental data were plotted using GraphPad Prism®. The results of the experiments are shown in Table 1.

TABLE 1

Activity of compounds 1-24, 27, and 29 against USP28 in Ubiquitin-Rhodamine 110 assay.

| Compound | USP28 activity |
|---|---|
| 1 | ++++ |
| 2 | +++ |
| 3 | +++ |
| 4 | ++ |
| 5 | + |
| 6 | ++ |
| 7 | + |
| 8 | +++ |
| 9 | + |
| 10 | +++ |
| 11 | ++++ |
| 12 | ++++ |
| 13 | ++ |
| 14 | ++++ |
| 15 | ++++ |
| 16 | ++++ |
| 17 | +++ |
| 18 | ++ |
| 19 | + |
| 20 | ++++ |
| 21 | ++++ |
| 22 | +++ |
| 23 | ++++ |
| 24 | ++++ |
| 27 | + |
| 29 | +++ |

IC50:
++++, <1 μM;
+++, 1-10 μM;
++, 10-100 μM;
+, >100 μM.

Example 2. Selectivity Profiling

Selectivity profiling (DUBProfiler™) was performed by Ubiquigent using the manufacturer's protocols. The results of the experiments are shown in FIG. 1.

Example 3. Competitive Activity-Based Protein Profiling (General Protocol)

Figure 2:
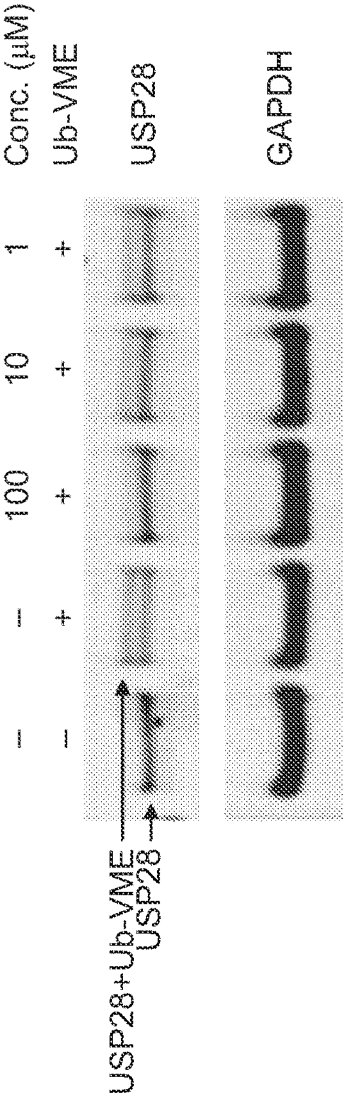
FIG. 2 shows a Western blot image demonstrating target engagement in K562 cells treated with compound 1 at various concentrations in the presence and absence of Ub-VME (Ubiquitin-vinylmethylester). K562 cells were lysed and treated with indicated concentrations of compound 1 for 1 h followed by incubation with Ub-VME. Ub-VME covalently modifies USP28, resulting in higher MW band observed by Western blot. Compound 1, binding to USP28, prevents labeling of USP28 by the covalent Ub-VME probe, which results in in the formation of a lower MW band for native USP28.
Figure 3:
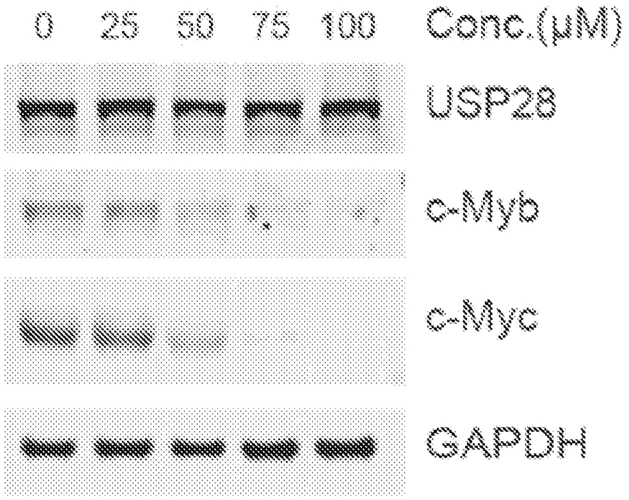
FIG. 3 shows C-Myc and C-Myb Western blots in NOMO-1 cells treated with compound 1 at various concentrations.
Figure 4:
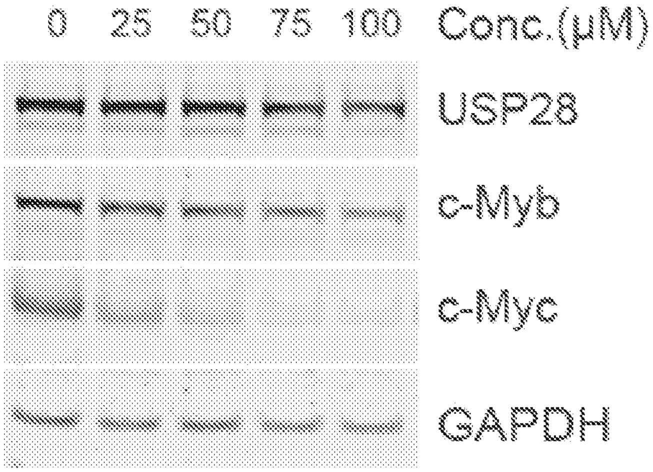
FIG. 4 shows C-Myc and C-Myb Western blots in K562 cells treated with compound 1 at various concentrations.
Figure 5:
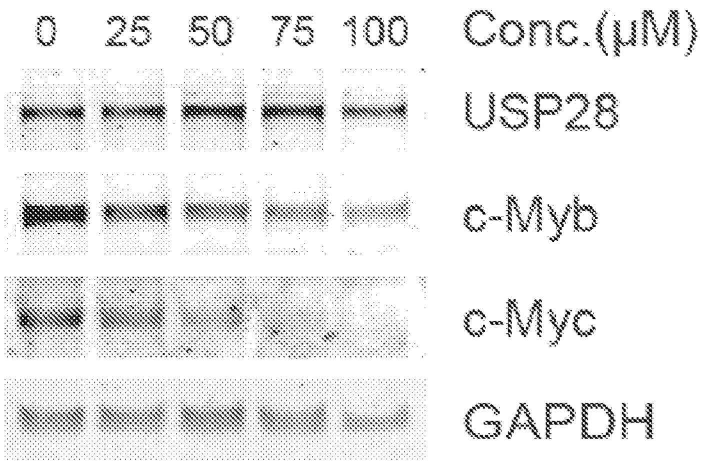
FIG. 5 shows C-Myc and C-Myb Western blots in MOLM14 cells treated with compound 1 at various concentrations.
Figure 6:
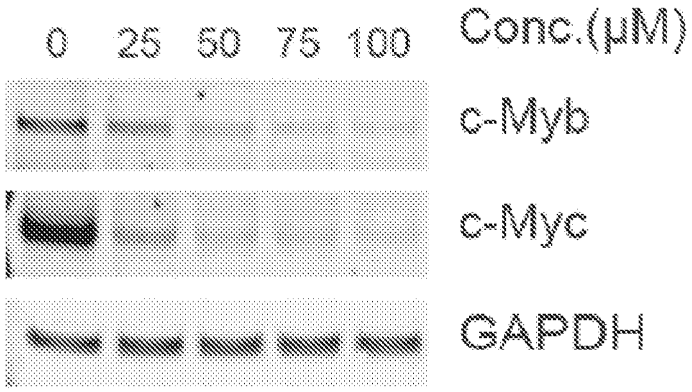
FIG. 6 shows C-Myc and C-Myb Western blots in MM1S cells treated with compound 1 at various concentrations.
Figure 7:
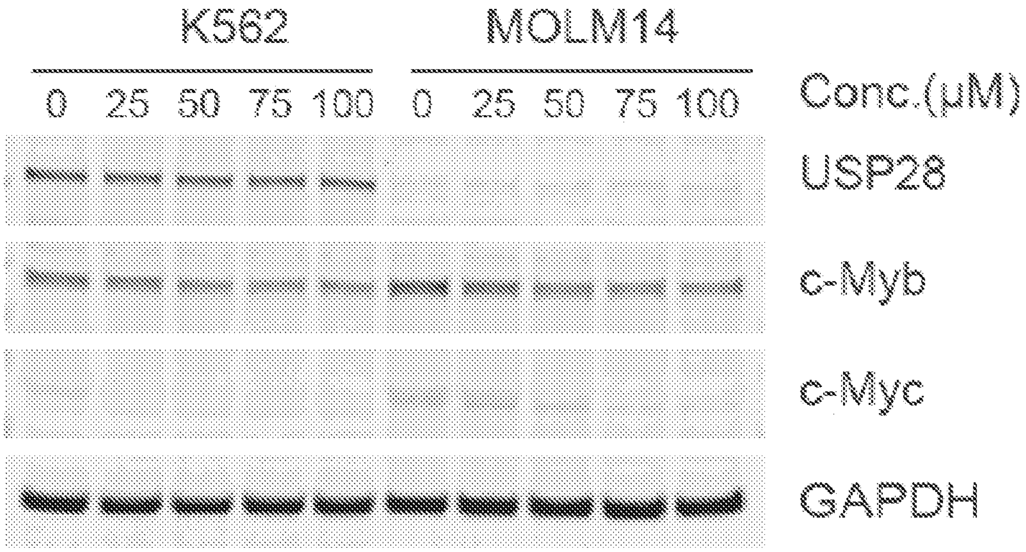
FIG. 7 shows C-Myc and C-Myb Western blots in K562 and MOLM14 cells treated with compound 1 at various concentrations.

Cells were pelleted, washed with PBS buffer, lysed on ice (20 mM Tris pH 8, 150 mM NaCl, 1% NP-40, 10% glycerol, 1 mM TCEP, phosphatase inhibitor cocktails (Sigma P5726 and Calbiochem 524624), and protease inhibitors (pepstatin, leupeptin, PMSF, and aprotinin), and clarified by centrifugation. Protein content was quantified by BCA and diluted to 2 mg/mL in lysis buffer. Compounds were added at desired concentrations and incubated at room temperature for 30 minutes. Samples were then supplemented with 2 uM HA-Ub-VS and incubated at room temperature with shaking for 15 minutes. Reactions were quenched with 4×LDS sample buffer (Thermo Fisher B0007) supplemented with 10% BME, vortexed vigorously, and heated to 95° C. for 5 minutes. Samples were resolved by SDS-PAGE and analyzed by Western blot with the indicated antibodies. The results of the experiments are shown in FIG. 2.

Example 4. Cell Treatment with Specific Inhibitors Followed by Western Blotting for Putative USP28 Targets Myc and Myb Along with USP28 Levels in Different Cell Lines Cell Lines Nomo-1 was obtained from Dr. Gary Gilliland. The other cell lines were originally obtained from ATCC, where *Mycoplasma* contamination was tested, and cell characterization was performed using polymorphic short tandem repeat (STR) profiling. All cell lines were cultured at a concentration of 2×105 to 5×105 cells/mL in RPIM 1640 (Life Technologies) supplemented with 10% fetal bovine serum (Sigma), 2% L-glutamine (Gibco) and 1% penicillin-streptomycin (Gibco).

Compounds Treatment and Immunoblotting

AML cell lines were treated for 3 h with inhibitors. Cells were harvested and lysed in RIPA buffer (Tris pH 7.4 50 mM, NaCl 150 mM, NP-40 1%, SDS 0.1%, EDTA 2 μM) containing HALT protease inhibitor cocktail (Thermo Fisher). The cell lysates were quantified using a BCA Protein Assay Kit (Thermo Scientific). The cell lysates (~15 μg protein) were separated by SDS-PAGE, transferred to a nitrocellulose membrane, blocked in milk, and treated with antibodies. After washing, the membrane was treated with a 780-nm IRdye goat anti-rabbit IgG (Licor) and imaged with an Odyssey scanner (Licor).

Compounds.

DUB inhibitors were synthesized according to published literature procedures. All inhibitors were reconstituted in DMSO (Sigma-Aldrich) at a stock concentration of 10 mM.

Antibodies.

Antibodies against the following proteins were used: USP28 (#4217, 1:1000), c-Myc (#5605, 1:1000), GAPDH (#8884, 1:1000), Actin (#5125, 1:1000) (Cell Signaling Technology). c-Myb (Santa Cruz, sc-74512, 1:200).

The results of the experiments are shown in FIGS. 3-7.

Synthetic Procedures

All commercially available starting materials were purchased from Sigma Aldrich, Fisher Scientific, Oakwood Chemical and Combi Block. All reagents were used as received without further purification. Known compounds were synthesized according to published literature procedures and any modifications are noted. Anhydrous solvents, such as tetrahydrofuran (THF), diethyl ether, dichloromethane (DCM), dimethyl formamide (DMF), dimethylsulfoxide (DMSO), 1,4-dioxane, and toluene (PhMe) were purchased from Fisher Scientific, and used as received. If necessary, air or moisture sensitive reactions were carried out under an inert atmosphere of nitrogen.

Removal of solvents was accomplished on a Büchi R-300 rotary evaporator and further concentration was done under vacuum generated by a Welch 1400B-01 vacuum line, and Labconco FreeZone 6 plus system. Purification of compounds was performed by normal phase column chromatography using Teledyne CombiFlash chromatography system, and/or reverse phase chromatography on Waters Micromass ZQ preparative system with SunFire® Prep C18 OBD™ 5 μM column. Purity of the compounds was analyzed on Waters Acquity UPLC system. Analytical thin layer chromatography (TLC) plates were purchased from Fisher Scientific (EMD Millipore TLC Silica Ge160 F254). Visualization was accomplished by irradiation under UV light (254 nm).

All $^{1}H$-NMR spectra were recorded at 298K on a Bruker ARX 500 (500 MHz) spectrometer. $^{13}C$-NMR spectra were recorded on a Bruker ARX 500 (126 MHz) spectrometer.

Samples were dissolved in $CDCl_3$, DMSO-d6, or $CD_3OD$. The spectra were referenced to the residual solvent peak (chloroform-d: 7.26 ppm for $^1$H-NMR and 77.16 ppm for $^{13}$C-NMR; DMSO-d6: 2.50 ppm for $^1$H-NMR and 39.25 ppm for $^{13}$C-NMR, $CD_3OD$: 3.31 ppm for $^1$H NMR and 49.00 ppm for 13C NMR or tetramethylsilane (TMS) as the internal standard). NMR data for each peak is reported as the chemical shift, multiplicity (s=singlet, d=doublet, t=triplet, q=quartet, m=multiplet, br=broad peak), coupling constants (Hz), and number of protons. Mass spectrometry (LCMS) data were obtained on Waters Acquity UPLC system in positive ESI mode.

Example 5. Exemplary Syntheses of Compounds of the Disclosure

Compound 1

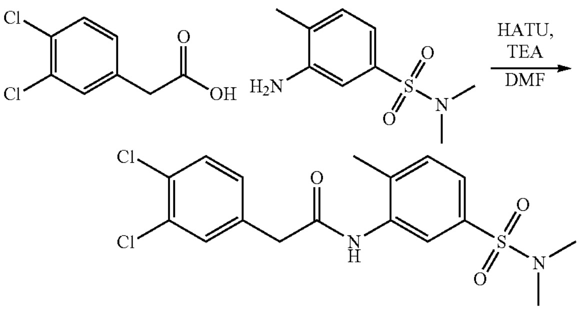

3,4-Dichlorophenylacetic acid (100.4 mg, 0.49 mmol) was combined with HATU (226.4 mg, 0.60 mmol) and suspended in DMF (3 mL). TEA (204.9 μL, 1.47 mmol) was added to the mixture, and the resulting reaction mixture was allowed to stir at room temperature for about 15 minutes. 3-Amino-N,N-4-trimethylbenzene-1-sulfonamide (108.8 mg, 0.51 mmol) was added to the reaction mixture. The resulting mixture was allowed to stir at room temperature for 42 hours. The reaction mixture was diluted with ethyl acetate, and washed with water and brine. The organic layer was collected, dried over anhydrous sodium sulfate, filtered, and concentrated in vacuo. The crude material was purified via silica gel chromatography (0-100% ethyl acetate: hexanes) to afford pure compound 1 as a light brown powder (41.7 mg, 21%). LCMS (ESI) m/z=400.87 $[M+H]^+$. $^1$H NMR (500 MHz, Methanol-$d_4$) δ 7.86 (d, J=1.9 Hz, 1H), 7.57 (d, J=2.1 Hz, 1H), 7.55-7.45 (m, 3H), 7.32 (dd, J=8.3, 2.1 Hz, 1H), 3.78 (s, 2H), 2.67 (s, 6H), 2.31 (s, 3H).

Precursor A

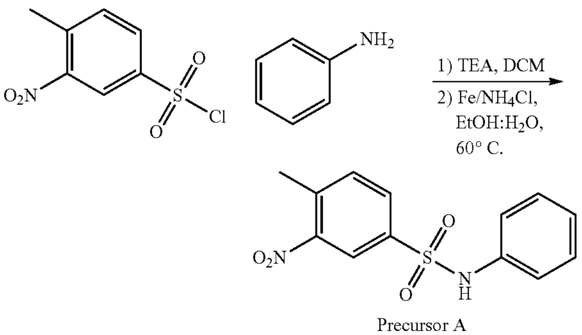

Precursor A 4-methyl-3-nitrobenzenesulfonyl chloride (235.7 mg, 1.0 mmol) was suspended in dichloromethane (5 mL). Aniline (91.2 uL, 1.0 mmol) and TEA (167.3 uL, 1.2 mmol) were then added to the reaction mixture, which was allowed to stir at room temperature for 90 minutes. The reaction was concentrated to dryness under $N_2$. The intermediate was then combined with iron powder (564.3 mg, 10.1 mmol) and $NH_4Cl$ (535.9 mg, 10.0 mmol). The resulting mixture was suspended in a 1:1 mixture of ethanol:water (8 mL total) and heated to 60° C. for 22 hours. The reaction mixture was removed from heat and filtered over Celite® to remove the iron powder. Ethanol was then removed in vacuo. Saturated sodium bicarbonate solution was then added to the reaction mixture to adjust the pH to ~8, and the reaction mixture was extracted with ethyl acetate. The organic fractions were combined, dried over anhydrous sodium sulfate, filtered, and concentrated in vacuo. The crude material was used in the subsequent coupling reactions without further purification (127.6 mg, 49%).

Compound 2

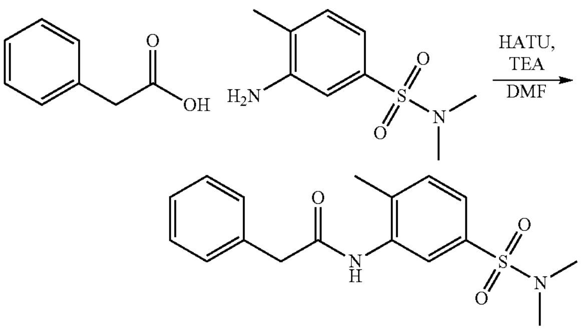

Phenylacetic acid (70.9 mg, 0.52 mmol) and HATU (237.2 mg, 0.62 mmol) were combined and suspended in DMF (2 mL). To the reaction was added TEA (217.4 μL, 1.56 mmol). The reaction mixture was stirred at room temperature for 10 minutes. 3-Amino-N,N-4-trimethylbenzene-1-sulfonamide (110.1 mg, 0.52 mmol) was then added to the reaction mixture, which was allowed to stir at room temperature for 6 h. The reaction mixture was diluted with ethyl acetate and washed with water and brine. The organic layer was collected, dried over anhydrous sodium sulfate, filtered, and concentrated in vacuo. The crude material was purified via silica gel chromatography (0-100% ethyl acetate:hexanes) to afford pure compound 2. LCMS (ESI) m/z=332.67 [M+H]+. $^1$H NMR (500 MHz, Methanol-$d_4$) δ 7.86 (d, J=2.0 Hz, 1H), 7.51 (dd, J=8.0, 1.9 Hz, 1H), 7.46 (d, J=8.0 Hz, 1H), 7.42-7.32 (m, 4H), 7.31-7.25 (m, 1H), 3.77 (s, 2H), 2.66 (s, 6H), 2.27 (s, 3H).

Compound 3

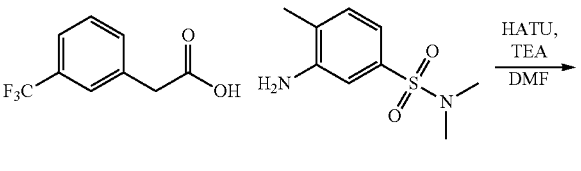

-continued

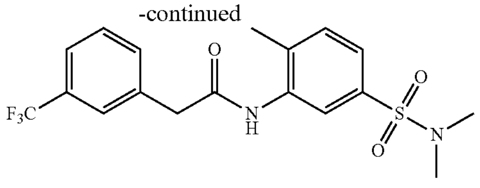

3-Trifluoromethylphenylacetic acid (102.0 mg, 0.50 mmol) and HATU (228.6 mg, 0.50 mmol) were combined and suspended in DMF (2 mL). To the reaction was added TEA (348.5 μL, 2.5 mmol), and the mixture was allowed to stir at room temperature for 30 minutes. 3-Amino-N,N-4-trimethylbenzene-1-sulfonamide (107.8 mg, 0.50 mmol) was added to the mixture, and the mixture was allowed to stir at room temperature for 24 h. The reaction mixture was diluted with ethyl acetate and washed with water and brine. The organic layer was collected, dried over anhydrous sodium sulfate, filtered, and concentrated in vacuo. The crude material was purified via silica gel chromatography (0-100% ethyl acetate:hexanes) to afford pure compound 3 (7.2 mg, 3.6%). LCMS (ESI) m/z=400.87 [M+H]+. $^1$H NMR (500 MHz, Chloroform-d) δ 8.23-8.15 (m, 1H), 7.68-7.51 (m, 4H), 7.45 (dd, J=7.9, 1.9 Hz, 1H), 7.28 (s, 1H), 7.13 (s, 1H), 3.85 (s, 2H), 2.70 (s, 6H), 2.09 (s, 3H).

Compound 4

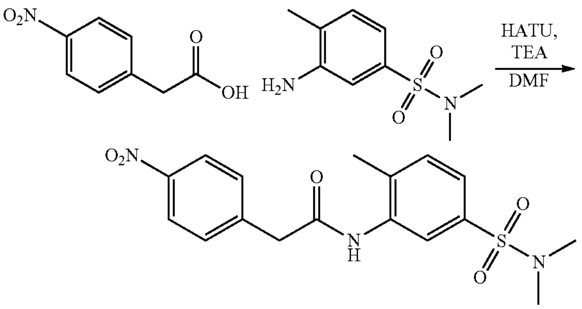

4-Nitrophenylacetic acid (90.9 mg, 0.50 mmol) and HATU (289.5 mg, 0.76 mmol) were combined and suspended in DMF (2 mL). To the reaction was added TEA (348.5 μL, 2.5 mmol), and the mixture was allowed to stir at room temperature for 30 minutes. 3-Amino-N,N-4-trimethylbenzene-1-sulfonamide (106.8 mg, 0.50 mmol) was then added, and the mixture was allowed to stir at room temperature for 24 h. The reaction mixture was diluted with ethyl acetate and washed with water and brine. The organic layer was collected, dried over anhydrous sodium sulfate, filtered, and concentrated in vacuo. The crude material was purified via silica gel chromatography (0-100% ethyl acetate:hexanes) to afford pure compound 4 (6.2 mg, 3.3%). LCMS (ESI) m/z=377.97 [M+H]+. $^1$H NMR (500 MHz, Methanol-$d_4$) δ 8.27-8.21 (m, 2H), 7.88 (d, J=2.0 Hz, 1H), 7.67-7.61 (m, 2H), 7.56-7.45 (m, 2H), 3.94 (s, 2H), 2.66 (s, 6H), 2.33 (s, 3H).

Compound 5

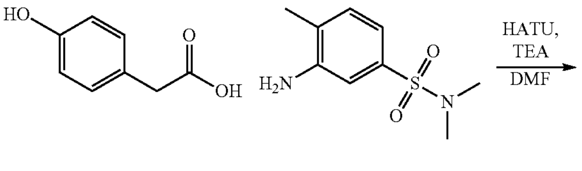

-continued

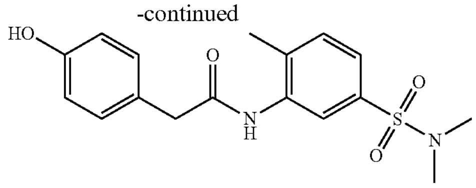

4-Hydroxyphenylacetic acid (77.3 mg, 0.51 mmol) and HATU (232.6 mg, 0.61 mmol) were combined and suspended in DMF (2 mL). To the reaction was added TEA (348.5 μL, 2.5 mmol), and the mixture was allowed to stir at room temperature for 30 minutes. 3-Amino-N,N-4-trimethylbenzene-1-sulfonamide (107.7 mg, 0.50 mmol) was added to the reaction mixture, and the mixture was allowed to stir at room temperature for 24 h. The reaction mixture was diluted with ethyl acetate and washed with water and brine. The organic layer was collected, dried over anhydrous sodium sulfate, filtered, and concentrated in vacuo. The crude material was purified via silica gel chromatography (0-100% ethyl acetate:hexanes) to afford pure compound 5 (26.0 mg, 14.9%). LCMS (ESI) m/z=348.97 [M+H]+.

Compound 6

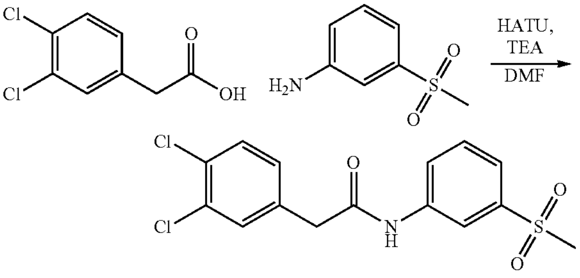

3,4-Dichlorophenylacetic acid (100.7 mg, 0.49 mmol) and HATU (225.3 mg, 0.59 mmol) were combined and suspended in DMF (2 mL). To the reaction was added TEA (341.5 μL, 2.45 mmol), and the mixture was allowed to stir at room temperature for 10 minutes. 3-Methylsulfonylaniline hydrochloric acid (103.2 mg, 0.50 mmol) was added to the reaction mixture, and the mixture was allowed to stir at room temperature for 22 h. The reaction mixture was diluted with ethyl acetate and washed with water and brine. The organic layer was collected, dried over anhydrous sodium sulfate, filtered, and concentrated in vacuo. The crude material was purified via silica gel chromatography (0-100% ethyl acetate:hexanes) followed by HPLC reverse phase purification to afford pure compound 6 (5.8 mg, 3.3%). LCMS (ESI) m/z=357.87 [M+H]+. $^1$H NMR (500 MHz, Chloroform-d) δ 8.08-8.01 (m, 1H), 7.90 (t, J=1.9 Hz, 1H), 7.86 (s, 1H), 7.66 (d, J=7.8 Hz, 1H), 7.52 (t, J=8.0 Hz, 1H), 7.49-7.42 (m, 2H), 7.21 (dd, J=8.2, 2.0 Hz, 1H), 3.70 (s, 2H), 3.07 (s, 3H).

Compound 7

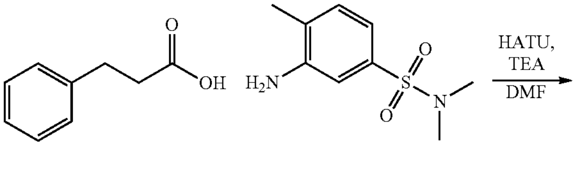

-continued

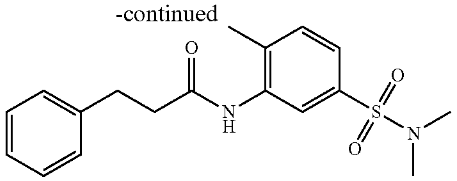

3-Phenylpropionic acid (78.9 mg, 0.53 mmol) and HATU (178.2 mg, 0.64 mmol) were combined and suspended in DMF (2 mL). To the reaction was added TEA (369.4 μL, 2.65 mmol) followed by 3-amino-N,N-4-trimethylbenzene-1-sulfonamide (114.1 mg, 0.53 mmol). The reaction was stirred at 60° C. for 22 h. The reaction mixture was diluted with ethyl acetate and washed with water and brine. The organic layer was collected, dried over anhydrous sodium sulfate, filtered, and concentrated in vacuo. The crude material was purified via silica gel chromatography (0-100% ethyl acetate:hexanes) to afford pure compound 7 (64.4 mg, 35.2%). LCMS (ESI) m/z=347.17 [M+H]+.

Compound 8

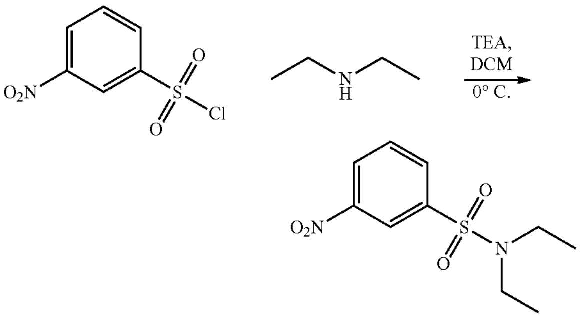

8-1

3-Nitrobenzenesulfonyl chloride (222.0 mg, 1.0 mmol) was suspended in DCM (5 mL) and the reaction mixture was placed in an ice bath. To the reaction was added a mixture of diethylamine (103.5 μL, 1.0 mmol) and TEA (167.3 μL, 1.2 mmol) dropwise. The reaction was stirred at 0° C. for 1 hour. The reaction mixture was diluted with DCM and washed with water and brine. The organic layer was collected, dried over anhydrous sodium sulfate, filtered, and concentrated in vacuo. The crude material, compound 8-1, was carried onto the next step without further purification.

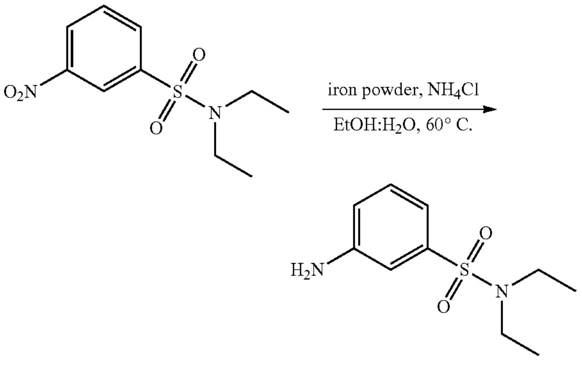

8-2

Compound 8-1 (209.7 mg, 0.81 mmol) was combined with iron powder (455.0 mg, 8.1 mmol) and ammonium chloride (435.0 mg, 8.1 mmol) and suspended in 1:1 EtOH:$H_2O$ (8 mL total). The reaction was stirred at 60° C. for 3 hours. The reaction was filtered over Celite® to remove iron powder and the filtrate was concentrated in vacuo. The crude product, compound 8-2, was carried onto the next step without further purification

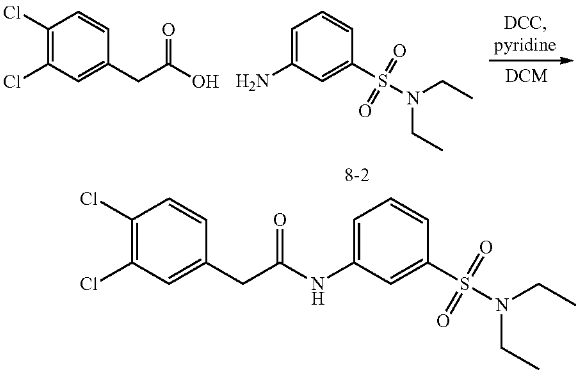

8-2

8

3,4-dichlorophenylacetic acid (383.6 mg, 1.87 mmol) and DCC (390.6 mg, 0.64 mmol) were combined and suspended in DCM (5 mL) followed by addition of pyridine (153.1 μL, 1.88 mmol). The reaction was stirred at room temperature for 5 minutes and compound 8-2 (213.5 mg, 1.94 mmol) was added to the mixture. The reaction was stirred at room temperature for 18 h. The reaction mixture was filtered, and the precipitate was purified via HPLC. Fractions containing the desired product were extracted with DCM, washed with water and brine and then repurified via silica gel chromatography (0-100% ethyl acetate:hexanes) to afford pure compound 8 (13.5 mg, 1.7%). LCMS (ESI) m/z=415.17 [M+H]+. $^1H$ NMR (500 MHz, Chloroform-d) δ 8.25 (s, 1H), 8.08-7.96 (m, 1H), 7.82 (t, J=2.0 Hz, 1H), 7.53-7.39 (m, 4H), 7.22 (dd, J=8.2, 2.1 Hz, 1H), 3.69 (s, 2H), 3.24 (q, J=7.1 Hz, 4H), 1.13 (t, J=7.1 Hz, 6H).

Compound 9

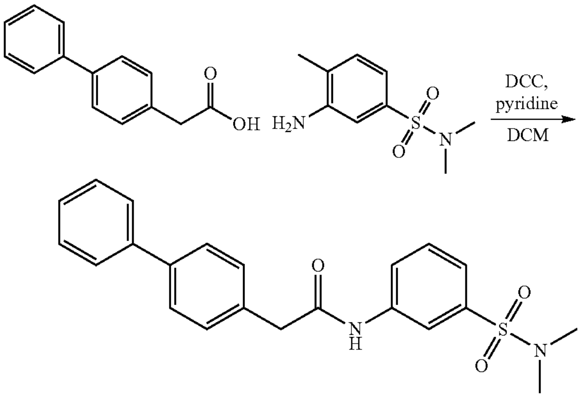

4-Biphenylacetic acid (215.9 mg, 1.02 mmol) and DCC (207.1 mg, 1.0 mmol) were combined and suspended in DCM (5 mL) followed by addition of pyridine (80.5 μL, 1.0 mmol). The reaction was stirred at room temperature for 5 minutes and 3-amino-N,N-4-trimethylbenzene-1-sulfonamide (108.7 mg, 0.51 mmol) was added to the mixture. The reaction was stirred at room temperature for 2.5 h. The reaction mixture was then quenched with saturated sodium bicarbonate solution and extracted with DCM. The organic fractions were combined and dried over anhydrous sodium sulfate, filtered, and concentrated in vacuo. The crude material was purified via silica gel chromatography (0-100% ethyl acetate:hexanes) followed by repurification via silica gel chromatography (0-10% methanol:dichloromethane) to afford pure compound 9 (77.7 mg, 37.2%). LCMS (ESI) m/z=409.27 [M+H]+. $^{1}$H NMR (500 MHz, DMSO-d6) δ 9.74 (s, 1H), 7.92 (d, J=2.0 Hz, 1H), 7.69-7.61 (m, 4H), 7.51-7.39 (m, 6H), 7.39-7.32 (m, 1H), 3.79 (s, 2H), 2.58 (s, 6H), 2.32 (s, 3H).

Compound 10

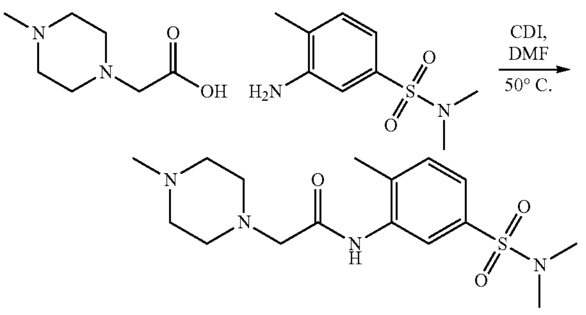

(4-Methyl-piperazin-1-yl)acetic acid (81.3 mg, 0.51 mmol) was combined with CDI (108.7 mg, 0.67 mmol) and suspended in DMF (2 mL). The reaction was stirred at 50° C. for 15 minutes, at which point 3-amino-N,N-4-trimethylbenzene-1-sulfonamide (163.0 mg, 0.76 mmol) was added to the mixture. The reaction was then stirred at 50° C. for 216 h. The reaction mixture was diluted with ethyl acetate and washed with water and brine. The organic layer was collected, dried over anhydrous sodium sulfate, filtered, and concentrated in vacuo. Purification via HPLC afforded compound 10 (32.1 mg, 17.7%). LCMS (ESI) m/z=355.07 [M+H]+. $^{1}$H NMR (500 MHz, Methanol-d$_4$) δ 8.08 (d, J=2.0 Hz, 1H), 7.58-7.42 (m, 2H), 4.90 (s, 6H), 3.49 (s, 2H), 3.42 (s, 3H), 3.05 (s, 3H), 2.94 (s, 3H), 2.38 (s, 3H), 1.30 (s, 2H).

Compound 11

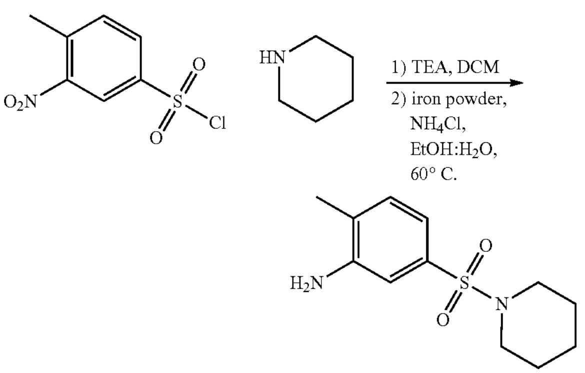

11-1

4-Methyl-3-nitrobenzenesulfonyl chloride (237.6 mg, 1.01 mmol) was suspended in DCM (5 mL). To the reaction were added piperidine (99.8 µL, 1.01 mmol) and TEA (168.9 µL, 1.21 mmol). The reaction mixture was stirred at room temperature for 3 h. The reaction mixture was concentrated under $N_2$ and used in the second step without further purification and assuming theoretical yield. The crude intermediate was combined with iron powder (563.0 mg, 10.08 mmol) and ammonium chloride (534.0 mg, 9.98 mmol), and the reaction mixture was suspended in a 1:1 mixture of EtOH and $H_2O$ (8 mL total). The reaction was stirred at 60° C. for 18 h. The reaction was filtered over Celite® to remove iron powder and concentrated in vacuo. The crude material, compound 11-1, was used in the next step without further purification.

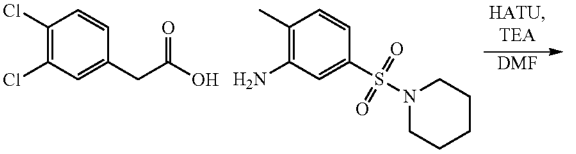

11-1

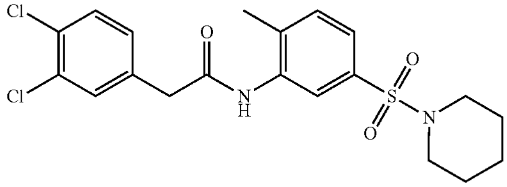

11

3,4-Dichlorophenylacetic acid (41.8 mg, 0.20 mmol) and HATU (97.7 mg, 0.26 mmol) were combined and suspended in DMF (1 mL). To the reaction was added TEA (118.5 µL, 0.85 mmol). The reaction was stirred at room temperature for 5 minutes. Compound 11-1 (42.9 mg, 0.17 mmol) was added to the reaction mixture, and the mixture was allowed to stir at room temperature for 72 h. The reaction mixture was diluted with ethyl acetate and washed with water and brine. The organic layer was collected, dried over anhydrous sodium sulfate, filtered, and concentrated in vacuo. The crude material was purified via silica gel chromatography (0-100% ethyl acetate:hexanes) followed by HPLC to afford pure compound 11 (24.1 mg, 27.3%). LCMS (ESI) m/z=441.18 [M+H]+. $^{1}$H NMR (500 MHz, Chloroform-d) δ 8.19-8.09 (m, 1H), 7.54-7.39 (m, 3H), 7.29 (s, 1H), 7.23 (dd, J=8.2, 2.1 Hz, 1H), 7.04 (s, 1H), 3.74 (s, 2H), 3.00 (t, J=5.5 Hz, 4H), 2.15 (s, 3H), 1.63 (p, J=5.9 Hz, 4H), 1.41 (td, J=5.9, 5.2, 2.5 Hz, 2H).

Compound 12

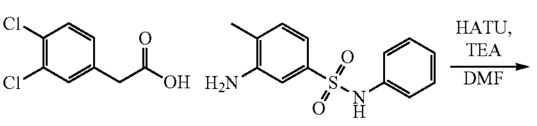

Precursor A

-continued

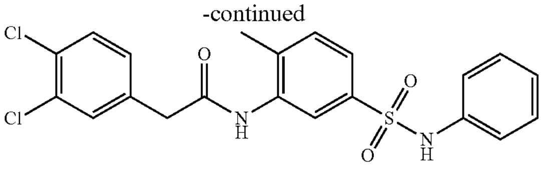

3,4-Dichlorophenylacetic acid (48.2 mg, 0.24 mmol), HATU (108.7 mg, 0.29 mmol) and Precursor A (49.9 mg, 0.19 mmol) were combined and suspended in DMF (1 mL). To the reaction was added TEA (132.4 μL, 0.95 mmol). The reaction was stirred at 60° C. for 67 h. The reaction mixture was diluted with ethyl acetate and then washed with water and brine. The organic layer was collected, dried over anhydrous sodium sulfate, filtered, and concentrated in vacuo. The crude material was purified via silica gel chromatography (0-100% ethyl acetate:hexanes) followed by HPLC to afford pure compound 12 (26.8 mg, 24.9%). LCMS (ESI) m/z=449.08 [M+H]+. $^1H$ NMR (500 MHz, Chloroform-d) δ 8.37-8.29 (m, 1H), 7.49-7.42 (m, 2H), 7.41-7.33 (m, 1H), 7.24-7.01 (m, 9H), 3.72 (s, 2H), 2.08 (s, 3H).

Compound 13

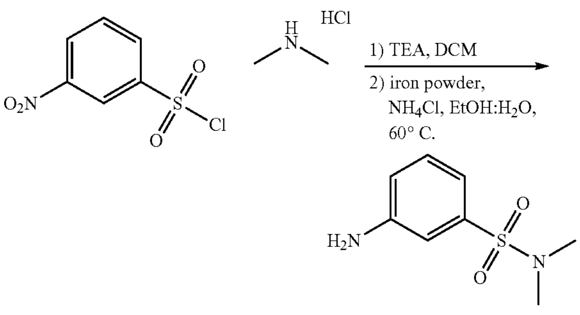

13-1

3-Nitrobenzenesulfonyl chloride (447.8 mg, 2.02 mmol) was suspended in DCM (5 mL). To the reaction was added dimethylamine hydrochloride (171.8 mg, 2.1 mmol) and TEA (844.6 μL, 6.06 mmol). The reaction mixture was stirred at room temperature for 1 h. The reaction was concentrated under $N_2$ and used in the second step without further purification and assuming theoretical yield. The crude intermediate was combined with iron powder (1128.7 mg, 20.2 mmol) and ammonium chloride (1080.5 mg, 20.2 mmol) and the reaction mixture was suspended in a 1:1 mixture of EtOH and $H_2O$ (8 mL total). The reaction was stirred at 60° C. for 14 h. The reaction was filtered over Celite® to remove iron powder and concentrated in vacuo. The crude material, compound 13-1, was used in the next step without further purification.

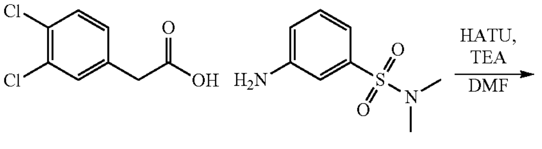

13-1

-continued

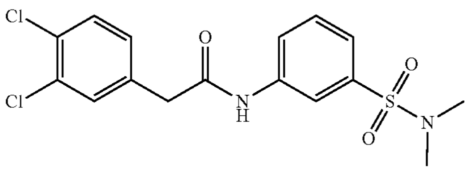

13

3,4-Dichlorophenylacetic acid (55.8 mg, 0.27 mmol), HATU (128.3 mg, 0.34 mmol) and compound 13-1 (45.1 mg, 0.23 mmol) were combined and suspended in DMF (1 mL). To the reaction was added TEA (156.9 μL, 1.13 mmol). The reaction was stirred at 60° C. for 22 h. The reaction mixture was diluted with ethyl acetate and then washed with water and brine. The organic layer was collected, dried over anhydrous sodium sulfate, filtered, and concentrated in vacuo. The crude material was purified via silica gel chromatography (0-100% ethyl acetate:hexanes) followed by HPLC to afford pure compound 13 (73.6 mg, 70.4%). LCMS (ESI) m/z=387.27 $[M+H]^+$.

Compound 14

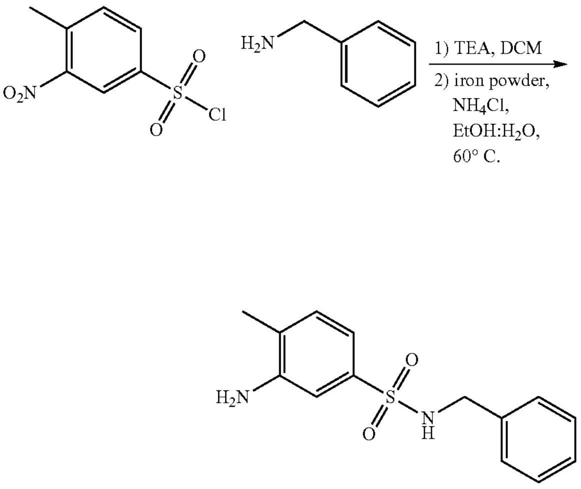

14-1

4-Methyl-3-nitrobenzenesulfonyl chloride (100.0 mg, 0.42 mmol) and benzylamine (48.1 μL, 0.44 mmol) were combined and suspended in DCM (2 mL). To the reaction was added TEA (175.6 μL, 1.26 mmol). The reaction mixture was stirred at room temperature for 46 h. The reaction was concentrated under $N_2$ and used in the second step without further purification and assuming theoretical yield. The crude intermediate was combined with iron powder (234.6 mg, 4.2 mmol) and ammonium chloride (224.7 mg, 4.2 mmol) and the reaction mixture was suspended in a 1:1 mixture of EtOH and $H_2O$ (4 mL total). The reaction was stirred at 60° C. for 4 h. The reaction was filtered over Celite® to remove iron powder and the filtrate was quenched with saturated sodium bicarbonate. The resulting mixture was extracted with EtOAc. The organic layer was collected, dry over anhydrous sodium sulfate, filtered, and concentrated in vacuo. The crude material, compound 14-1, was used in the next step without further purification.

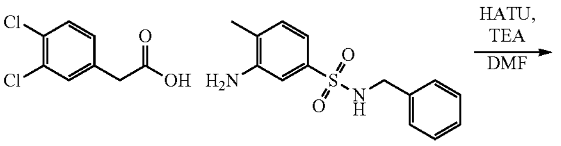

14-1

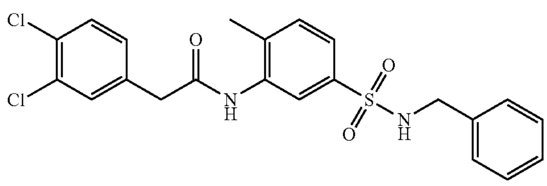

14

3,4-Dichlorophenylacetic acid (23.6 mg, 0.12 mmol), HATU (54.8 mg, 0.14 mmol) and compound 14-1 (26.5 mg, 0.096 mmol) were combined and suspended in DMF (1 mL). To the reaction was added TEA (66.9 µL, 0.48 mmol). The reaction was stirred at room temperature for 1 h. The reaction mixture was diluted with ethyl acetate and then washed with water and brine. The organic layer was collected, dried over anhydrous sodium sulfate, filtered, and concentrated in vacuo. The crude material was purified via silica gel chromatography (0-100% ethyl acetate:hexanes) followed by HPLC to afford pure compound 14 (22.8 mg, 40.8%). LCMS (ESI) m/z=465.08 [M+H]+.

Compound 15

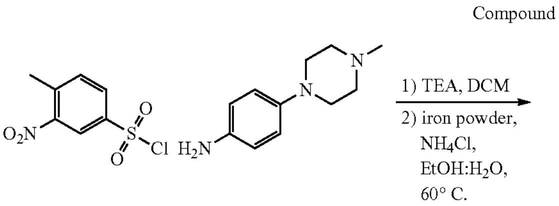

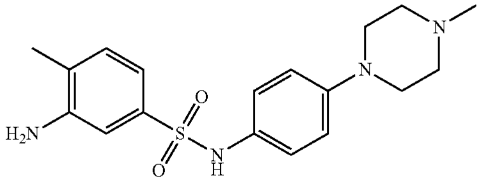

15-1

4-Methyl-3-nitrobenzenesulfonyl chloride (116.8 mg, 0.50 mmol) and 4-(4-methylpiperazino)aniline (95.5 mg, 0.50 mmol) were combined and suspended in DCM (2 mL). To the reaction was added TEA (104.5 µL, 0.75 mmol). The reaction mixture was stirred at room temperature for 3.5 h. The reaction was concentrated under $N_2$ and used in the second step without further purification and assuming theoretical yield. The crude intermediate was combined with iron powder (279.3 mg, 5.0 mmol) and ammonium chloride (267.5 mg, 5.0 mmol) and the reaction mixture was suspended in a 1:1 mixture of EtOH and $H_2O$ (4 mL total). The reaction was stirred at 60° C. for 17 h. The reaction was filtered over Celite® to remove iron powder and the filtrate was washed with saturated sodium bicarbonate, water and brine and extracted with ethyl acetate. The organic layer was collected, dried over anhydrous sodium sulfate, filtered, and concentrated in vacuo. The crude material, compound 15-1, was used in the next step without further purification.

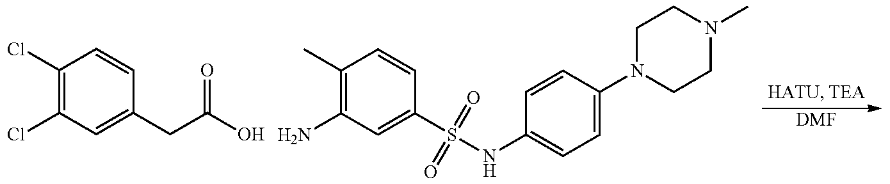

15-1

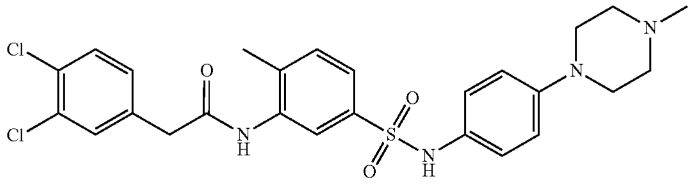

15

3,4-Dichlorophenylacetic acid (61.5 mg, 0.30 mmol), HATU (146.7 mg, 0.39 mmol) and compound 15-1 (54.2 mg, 0.15 mmol) were combined and suspended in DMF (1.5 mL). To the reaction was added TEA (104.9 μL, 0.75 mmol). The reaction was stirred at room temperature for 24 h. The reaction mixture was diluted with ethyl acetate and then washed with water and brine. The organic layer was collected, dried over anhydrous sodium sulfate, filtered, and concentrated in vacuo. The crude material was purified via silica gel chromatography (0-100% ethyl acetate:hexanes to 0-20% methanol:dichloromethane) to afford pure compound 15 (23.4 mg, 28.5%). LCMS (ESI) m/z=547.29 [M+H]+.

Compound 29

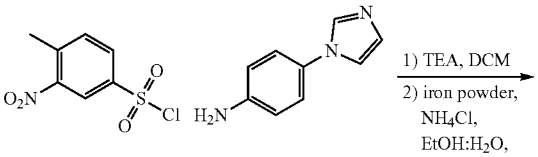

-continued

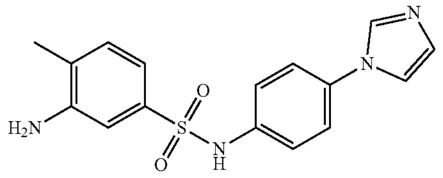

29-1

4-Methyl-3-nitrobenzenesulfonyl chloride (119.9 mg, 0.51 mmol) and 4-(4-methylpiperazino)aniline (79.6 mg, 0.50 mmol) were combined and suspended in DCM (2 mL). To the reaction was added TEA (104.5 μL, 0.75 mmol). The reaction mixture was stirred at room temperature for 3.5 h. The reaction was concentrated under nitrogen and used in the second step without further purification and assuming theoretical yield. The crude intermediate was combined with iron powder (279.3 mg, 5.0 mmol) and ammonium chloride (267.5 mg, 5.0 mmol) and the reaction mixture was suspended in a 1:1 mixture of EtOH and $H_2O$ (4 mL total). The reaction was stirred at 60° C. for 17 h. The reaction was filtered over Celite® to remove iron powder and the filtrate was washed with saturated sodium bicarbonate, water and brine and extracted with ethyl acetate. The organic layer was collected, dry over anhydrous sodium sulfate, filtered, and concentrated in vacuo. The crude material, compound 29-1, was used in the next step without further purification.

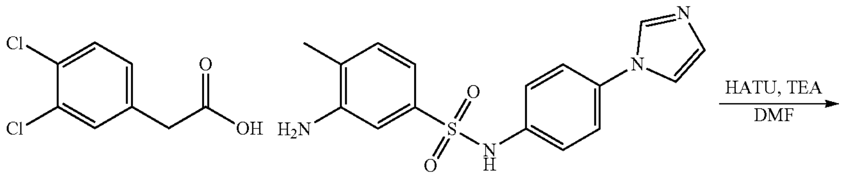

29-1

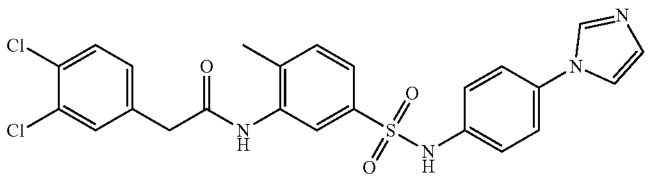

29

Compound 29-1 (61.2 mg, 0.19 mmol), 3,4-dichlorophenylacetic acid (78.1 mg, 0.38 mmol) and HATU (177.2 mg, 0.47 mmol) were combined and suspended in DMF (2 mL). TEA (130.0 μL, 0.93 mmol) was added to the reaction mixture, and the reaction was stirred at room temperature for 22 h. The reaction mixture was diluted with ethyl acetate and washed with saturated sodium bicarbonate, brine and water. The organic layer was collected, dried over anhydrous sodium sulfate, filtered, and concentrated in vacuo. The crude material was purified via silica gel chromatography (0-10% methanol:dichloromethane) to afford pure compound 29 (3.8 mg, 4.6%). LCMS (ESI) m/z=515.18 [M+H]+.

Compound 16

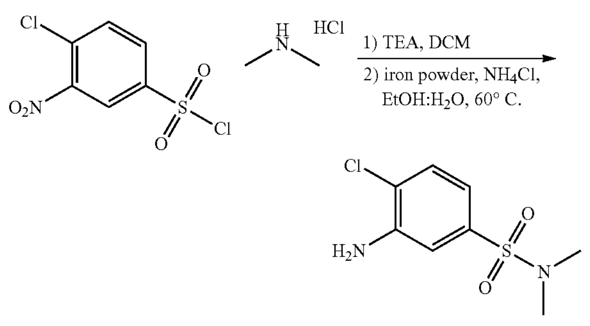

16-1

4-Chloro-3-nitrobenzenesulfonyl chloride (258.7 mg, 1.0 mmol) and dimethylamine hydrochloride (83.9 mg, 1.0 mmol) were combined and suspended in DCM (5 mL). To the reaction was added TEA (430.2 μL, 3.0 mmol). The reaction mixture was stirred at room temperature for 1 h. The reaction was concentrated under $N_2$ and used in the second step without further purification and assuming theoretical yield. The crude intermediate was combined with iron powder (560.7 mg, 10.0 mmol) and ammonium chloride (541.9 mg, 10.0 mmol) and the reaction mixture was suspended in a 1:1 mixture of EtOH and $H_2O$ (6 mL total). The reaction was stirred at 60° C. for 3 h. The reaction was filtered over Celite® to remove iron powder and the filtrate was concentrated in vacuo. The crude material was purified via silica gel chromatography (0-100% ethyl acetate: hexanes) to afford the desired intermediate, compound 16-1.

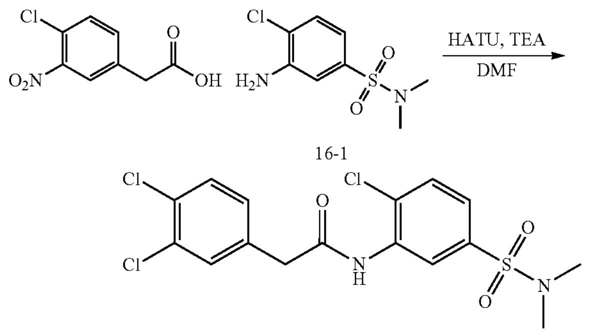

16-1

16

3,4-dichlorophenylacetic acid (184.5 mg, 0.90 mmol), HATU (422.6 mg, 1.11 mmol) and compound 16-1 (172.4 mg, 0.74 mmol) were combined and suspended in DMF (4 mL). To the reaction was added TEA (515.7 μL, 3.7 mmol). The reaction was stirred at room temperature for 21 h. The reaction mixture was diluted with ethyl acetate and then washed with water, saturated sodium bicarbonate and brine. The organic layer was collected, dried over anhydrous sodium sulfate, filtered, and concentrated in vacuo. The crude material was purified via silica gel chromatography (0-100% ethyl acetate:hexanes). Fractions containing desired product were repurified via HPLC to afford pure compound 16 (40.0 mg, 10.0%). LCMS (ESI) m/z=421.07 [M+H]+. $^1H$ NMR (500 MHz, Chloroform-d) δ 8.74 (d, J=2.0 Hz, 1H), 7.70 (s, 1H), 7.56-7.43 (m, 4H), 7.21 (dd, J=8.2, 2.2 Hz, 1H), 3.77 (s, 2H), 2.75 (s, 6H).

Compound 17

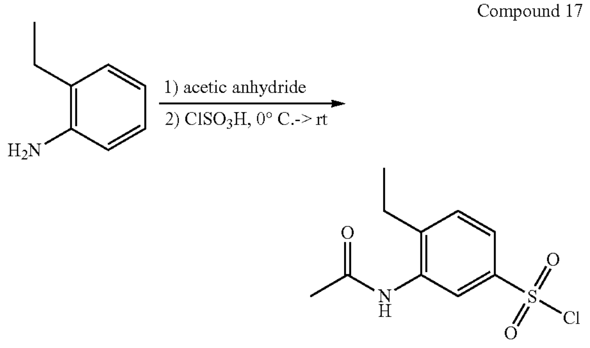

17-1

2-Ethylaniline (246.3 uL, 2.0 mmol) was diluted in acetic anhydride (1 mL). The reaction was stirred at room temperature for 1 h. The reaction was quenched with $H_2O$ and extracted with ethyl acetate. The organic fractions were combined and washed with saturated sodium bicarbonate and brine. The organic layer was collected, dried over anhydrous sodium sulfate, filtered, and concentrated in vacuo. The crude intermediate was then placed in an ice bath and chlorosulfonic acid (2.5 mL) was added to the mixture. The reaction was warmed to room temperature and stirred for 24 h. The reaction was quenched with cold water and extracted with ethyl acetate. The organic layers were combined, dried over anhydrous sodium sulfate, filtered, and concentrated in vacuo to afford compound 17-1 as a crude intermediate.

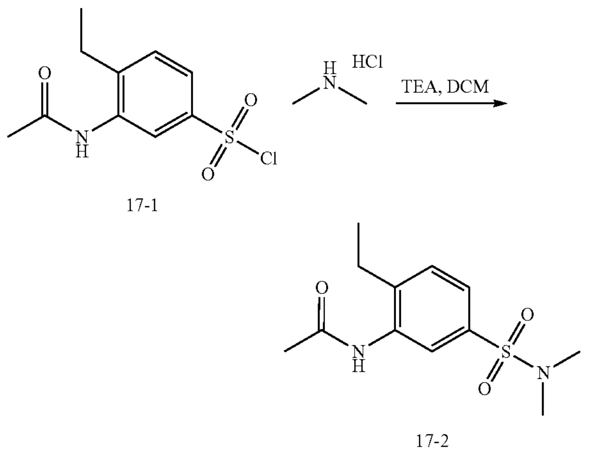

17-1

17-2

Compound 17-1 (2 mmol) was suspended in DCM (8 mL). To the reaction was added dimethylamine hydrochloride (163.6 mg, 2.0 mmol) followed by TEA (836.3 μL, 6.0 mmol). The reaction was stirred at room temperature for 2 h. The reaction was quenched with $H_2O$ and extracted with ethyl acetate. The organic layers were combined and washed with brine. The organic layer was then dried over anhydrous sodium sulfate, filtered, and concentrated in vacuo. The crude material was purified via silica gel chromatography (0-100% ethyl acetate:hexanes) to afford the desired intermediate, compound 17-2 (328.3 mg).

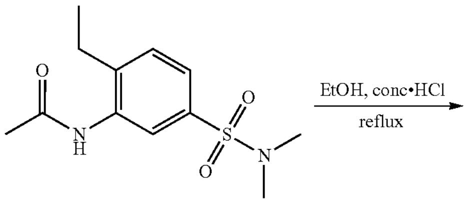

17-2

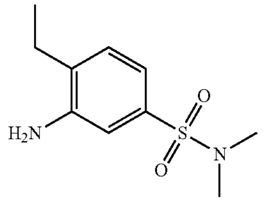

17-3

Compound 17-2 (151.4 mg, 0.56 mmol) was suspended in EtOH (2.5 mL) and concentrated hydrochloric acid was then added (0.5 mL). The reaction mixture was then refluxed for 3 h. The reaction mixture was concentrated in vacuo. The residue was resuspended in $H_2O$ and basified with 2M NaOH until pH ~9-10. The reaction mixture was then extracted with DCM. The organic fractions were combined, dried over anhydrous sodium sulfate, filtered, and concentrated in vacuo. The crude material was purified via silica gel chromatography (0-100% ethyl acetate:hexanes) to afford the desired intermediate, compound 17-3 (115.0 mg).

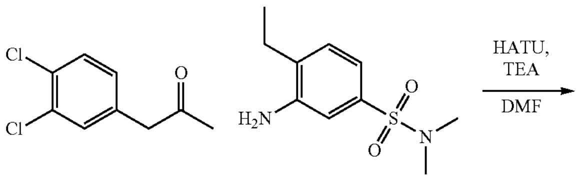

17-3

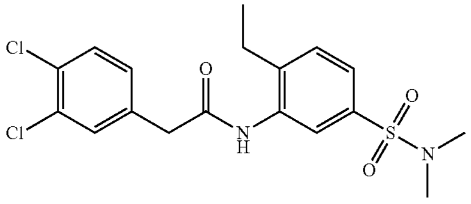

17

3,4-dichlorophenylacetic acid (154.2 mg, 0.75 mmol), HATU (386.9 mg, 1.02 mmol) and compound 17-3 (115.0 mg, 0.50 mmol) were combined and suspended in DMF (2 mL). To the reaction was added TEA (348.5 μL, 2.5 mmol). The reaction was stirred at room temperature for 1.5 h. The reaction mixture was diluted with ethyl acetate and then washed with water, saturated sodium bicarbonate and brine. The organic layer was collected, dried over anhydrous sodium sulfate, filtered, and concentrated in vacuo. The crude material was purified via silica gel chromatography (0-100% ethyl acetate:hexanes). Fractions containing desired product were repurified via HPLC to afford pure compound 17 (168.5 mg, 81.4%). LCMS (ESI) m/z=415.07 [M+H]+. $^1$H NMR (500 MHz, Methanol-$d_4$) δ 7.81 (d, J=2.0 Hz, 1H), 7.58 (td, J=4.0, 3.2, 1.9 Hz, 2H), 7.50 (dd, J=8.2, 2.1 Hz, 2H), 7.32 (dd, J=8.2, 2.1 Hz, 1H), 3.77 (s, 2H), 2.67 (s, 8H), 1.15 (t, J=7.6 Hz, 3H).

Compound 18

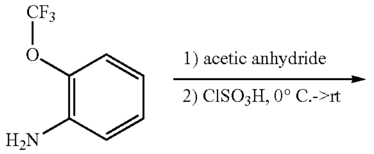

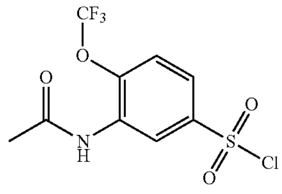

18-1

2-Trifluoromethoxyaniline (272.3 uL, 2.0 mmol) was diluted in acetic anhydride (1 mL). The reaction was stirred at room temperature for 1 h. The reaction was quenched with $H_2O$ and then extracted with ethyl acetate. The organic fractions were combined and washed with saturated sodium bicarbonate and brine. The organic layer was collected, dried over anhydrous sodium sulfate, filtered, and concentrated in vacuo. The crude intermediate was then placed in an ice bath and chlorosulfonic acid (2.5 mL) was added. The reaction was warmed to room temperature and stirred for 24 h. The reaction was quenched with cold water and extracted with ethyl acetate. The organic layers were combined, dried over anhydrous sodium sulfate, filtered, and concentrated in vacuo to afford compound 18-1 as a crude intermediate.

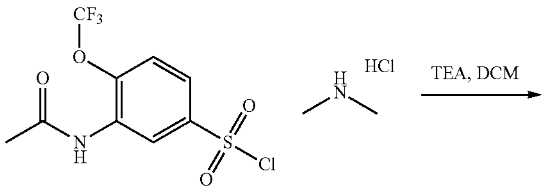

18-1

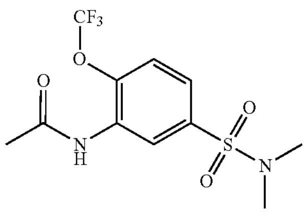

18-2

Compound 18-1 (2 mmol) was suspended in DCM (8 mL). To the reaction mixture was then added dimethylamine hydrochloride (163.0 mg, 2.0 mmol) followed by TEA (836.3 μL, 6.0 mmol). The reaction was stirred at room temperature for 2 h. The reaction was quenched with $H_2O$ and then extracted with ethyl acetate. The organic layers were combined and washed with brine. The organic layer was then dried over anhydrous sodium sulfate, filtered, and concentrated in vacuo. The crude material was purified via silica gel chromatography (0-100% ethyl acetate:hexanes) to afford the desired intermediate, compound 18-2 (36.6 mg).

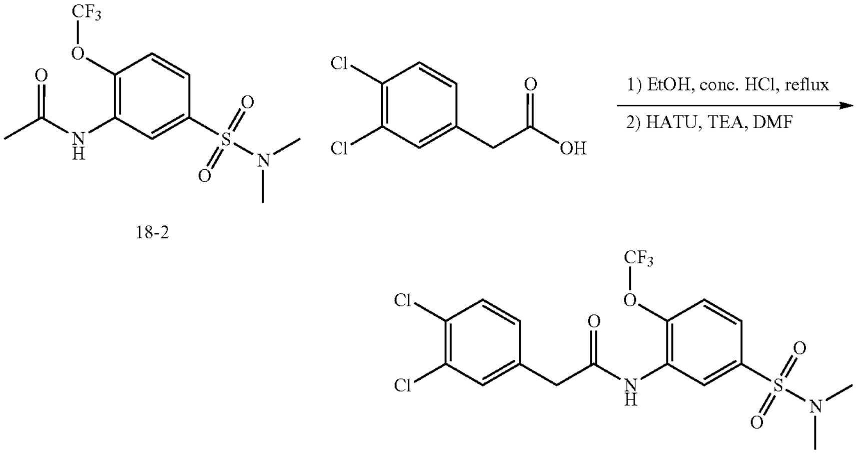

18-2

18

Compound 18-2 (36.6 mg, 0.11 mmol) was suspended in EtOH (1 mL) and concentrated hydrochloric acid was then added (0.5 mL). The reaction mixture was refluxed for 2 h. The reaction mixture was concentrated under nitrogen. The residue was resuspended in $H_2O$ and basified with 2M NaOH until pH ~9-10. The reaction was then extracted with DCM. The organic fractions were combined, dried over anhydrous sodium sulfate, filtered, and concentrated in vacuo. The crude material was carried forward to the next step without further purification. To the crude intermediate was added 3,4-dichlorophenylacetic acid (37.0 mg, 0.18 mmol) and HATU (83.7 mg, 0.22 mmol). The reaction was suspended in DMF (0.5 mL). To the reaction was added TEA (76.7 μL, 0.55 mmol). The reaction mixture was stirred at room temperature for 3.5 h. The reaction mixture was diluted with ethyl acetate and then washed with water, saturated sodium bicarbonate and brine. The organic layer was collected, dried over anhydrous sodium sulfate, filtered, and concentrated in vacuo. The crude material was purified via silica gel chromatography (0-100% ethyl acetate: hexanes). Fractions containing desired product were repurified via HPLC to afford pure compound 18 (12.9 mg, 24.9%). LCMS (ESI) m/z=471.08 [M+H]+.

-continued

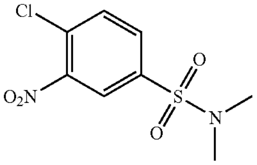

19-1

4-Chloro-3-nitrobenzenesulfonyl chloride (1287.7 mg, 5.03 mmol) and dimethylamine hydrochloride (414.8 mg, 5.09 mmol) were combined and suspended in DCM (20 mL). TEA (250.9 μL, 1.8 mmol) was added and the reaction mixture was stirred at room temperature for 2 h. The reaction mixture was diluted with ethyl acetate and then washed with saturated sodium bicarbonate, brine, and water. The organic layer was collected, dried over anhydrous sodium sulfate, filtered, and concentrated in vacuo. The crude material was purified via silica gel chromatography (0-100% ethyl acetate:hexanes) to afford compound 19-1 (1197.3 mg, 37.2%). $^1$H NMR (500 MHz, Chloroform-d) δ 8.25 (d, J=2.1 Hz, 1H), 7.90 (dd, J=8.4, 2.1 Hz, 1H), 7.75 (d, J=8.4 Hz, 1H), 2.79 (s, 6H).

Compound 19

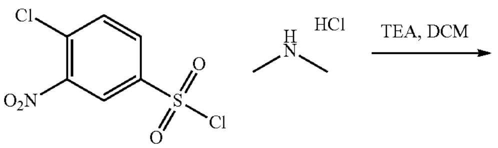

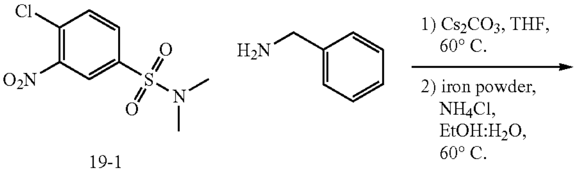

19-1

-continued

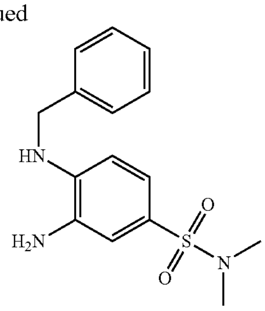

19-2

Compound 19-1 (151.6 mg, 0.57 mmol) and cesium carbonate (289.8 mg, 0.89 mmol) were combined and suspended in THF (2.5 mL). Benzylamine (125.1 μL, 1.15 mmol) was added to the reaction mixture, and the mixture was allowed to stir at 60° C. for 3 h. The reaction mixture was diluted with $H_2O$ and extracted with ethyl acetate. The combined organics were washed with brine, dried over anhydrous sodium sulfate, filtered, and concentrated in vacuo. To the crude material was then added iron powder (320.9 mg, 5.7 mmol) and ammonium chloride (304.9 mg, 5.7 mmol). The reaction mixture was suspended in a 1:1 mixture of $H_2O$:EtOH (4 mL total) and stirred at 60° C. for 2 h. The reaction was filtered over Celite® and the filtrate was concentrated in vacuo. Crude material, compound 19-2, was used in the next step without further purification.

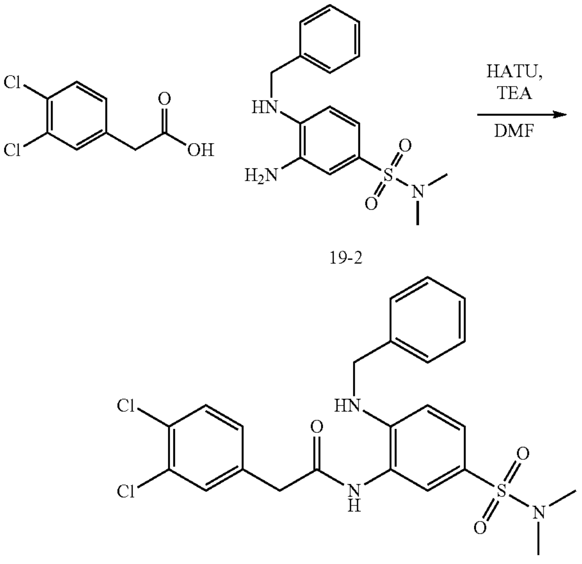

19-2

19

3,4-Dichlorophenylacetic acid (85.3 mg, 0.42 mmol), HATU (209.9 mg, 0.55 mmol) and compound 19-2 (84.2 mg, 0.27 mmol) were combined and suspended in DMF (1.5 mL). To the reaction was added TEA (191.0 μL, 1.37 mmol). The reaction was stirred at room temperature for 1.5 h. The reaction mixture was diluted with ethyl acetate and then washed with water, saturated sodium bicarbonate, and brine. The organic layer was collected, dried over anhydrous sodium sulfate, filtered, and concentrated in vacuo. The crude material was purified via silica gel chromatography (0-100% ethyl acetate:hexanes). Fractions containing desired product were repurified via HPLC to afford pure compound 19 (24.8 mg, 18.7%). LCMS (ESI) m/z=492.18 [M+H]+. $^1H$ NMR (500 MHz, DMSO-d6) δ 9.55 (s, 1H), 7.63 (d, J=2.0 Hz, 1H), 7.59 (d, J=8.2 Hz, 1H), 7.51 (d, J=2.3 Hz, 1H), 7.40-7.32 (m, 5H), 7.30 (dd, J=8.7, 2.3 Hz, 1H), 7.28-7.23 (m, 1H), 6.65 (d, J=8.7 Hz, 1H), 6.54 (t, J=5.9 Hz, 1H), 4.44 (d, J=5.9 Hz, 2H), 3.77 (s, 2H).

Compound 20

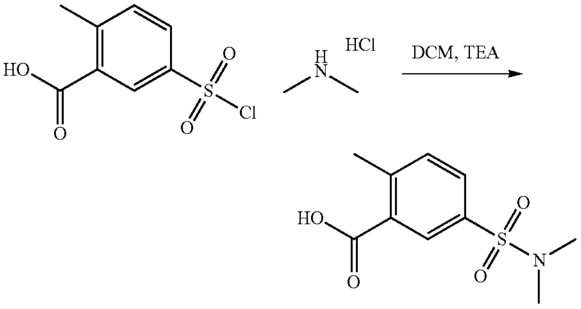

20-1

5-(chlorosulfonyl)-2-methylbenzenecarboxylic acid (80.0 mg, 0.34 mmol) and dimethylamine hydrochloride (33.4 mg, 0.41 mmol) were combined in DCM and TEA (94 μL, 0.67 mmol) was added to the resulting mixture. The reaction mixture was stirred at room temperature for 1 h. The reaction mixture was then quenched with saturated sodium bicarbonate solution and extracted with DCM. The organic fractions were combined and dried over anhydrous sodium sulfate, filtered, and concentrated in vacuo. The crude material was purified via silica gel chromatography to afford compound 20-1. LCMS (ESI) m/z=243.98 [M+H]+.

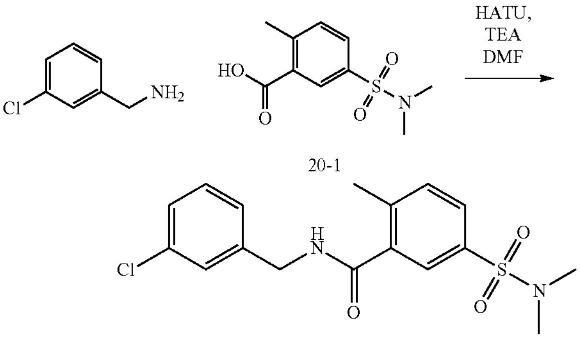

20-1

20

Compound 20-1 (20 mg, 0.09 mmol) was suspended in DMF (1 mL) and HATU (37.4 mg, 0.1 mmol) was then added followed by TEA (30 μL, 0.21 mmol). To the reaction was then added 3-chlorobenzylamine (12.2 mg, 0.09 mmol). The reaction was stirred at room temperature for 24 h. The reaction mixture was then quenched with saturated sodium bicarbonate solution and extracted with DCM. The organic fractions were combined and dried over anhydrous sodium sulfate, filtered, and concentrated in vacuo. The crude material was purified via silica gel chromatography to afford compound 20. LCMS (ESI) m/z=367.07 [M+H]+.

Compound 21

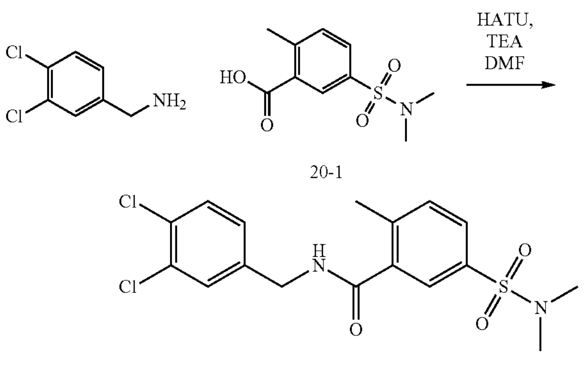

20-1

21

Compound 20-1 (20 mg, 0.09 mmol) was suspended in DMF (1 mL) and HATU (37.4 mg, 0.1 mmol) was then added followed by TEA (30 μL, 0.21 mmol). To the reaction was then added 3,4-dichlorobenzylamine (15.8 mg, 0.09 mmol). The reaction mixture was stirred at room temperature for 24 h. The reaction was then quenched with saturated sodium bicarbonate solution and extracted with DCM. The organic fractions were combined and dried over anhydrous sodium sulfate, filtered, and concentrated in vacuo. The crude material was purified via silica gel chromatography to afford compound 21. LCMS (ESI) m/z=401.17 [M+H]+.

Compound 22

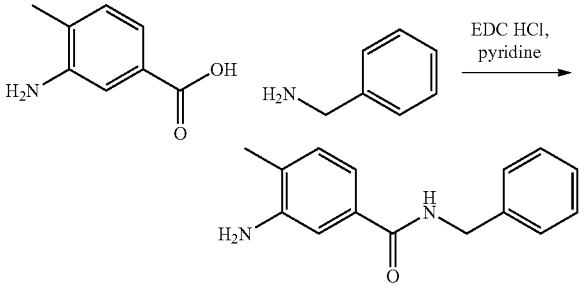

22-1

3-Amino-4-methylbenzoic acid (300.4 mg, 1.99 mmol), EDC hydrochloride (572.5 mg, 2.99 mmol) and benzylamine (217.1 μL, 1.99 mmol) were combined and suspended in pyridine (8 mL). The reaction was stirred at room temperature for 20 h. The reaction was removed from heat and diluted with ethyl acetate. The reaction mixture was washed with 1N HCl and brine. The organic layer was collected, dried over anhydrous sodium sulfate, filtered, and concentrated in vacuo. The crude material, compound 22-1, was used in the next step without further purification.

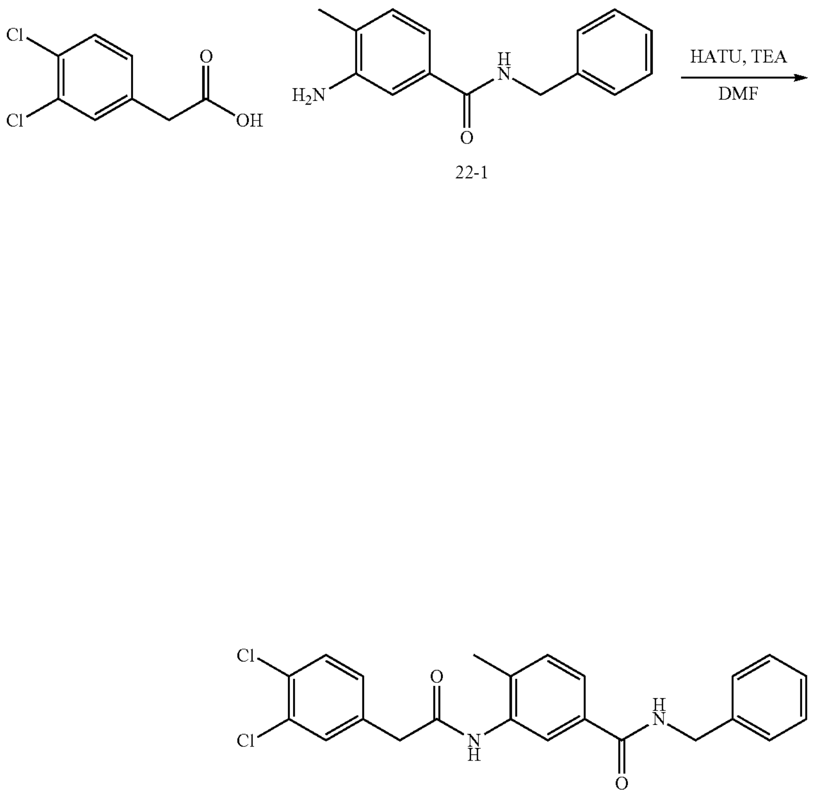

22-1

22

3,4-Dichlorophenylacetic acid (107.4 mg, 0.52 mmol) and HATU (299.0 mg, 0.79 mmol) were combined and suspended in DMF (2 mL). TEA (220.0 μL, 1.58 mmol) was then added and the reaction was stirred at room temperature for 10 minutes. Compound 22-1 (126.9 mg, 0.53 mmol) was then added and the reaction mixture was stirred at room temperature for 24 h. The reaction was diluted with ethyl acetate and washed with saturated bicarbonate and brine. The organic layer was collected, dried over anhydrous sodium sulfate, filtered, and concentrated in vacuo. The crude material was purified via silica gel chromatography (0-100% ethyl acetate:hexanes) to afford pure compound 22 (139.2 mg, 62.6%). LCMS (ESI) m/z=426.97 [M+H]+. $^{1}$H NMR (500 MHz, DMSO-d6) δ 9.67 (s, 1H), 8.97 (t, J=6.0 Hz, 1H), 7.88 (d, J=1.9 Hz, 1H), 7.68-7.57 (m, 3H), 7.37-7.27 (m, 6H), 7.25-7.20 (m, 1H), 4.45 (d, J=6.0 Hz, 2H), 3.73 (s, 2H), 2.21 (s, 3H).

Compound 23

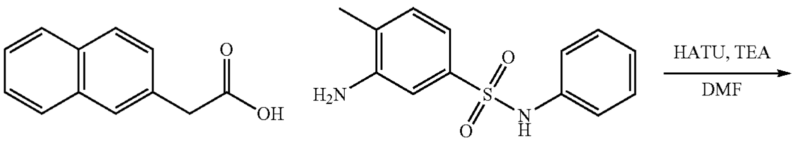

Precursor A

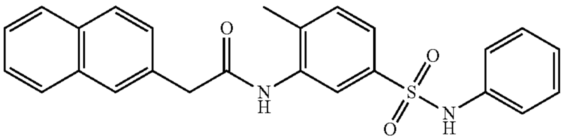

2-Naphthylacetic acid (59.2 mg, 0.32 mmol) and HATU (161.2 mg, 0.42 mmol) were combined and dissolved in DMF (2 mL). TEA (117.1 μL, 0.84 mmol) was then added and the reaction was stirred at room temperature for 15 minutes. To the reaction was then added Precursor A (74.6 mg, 0.28 mmol) and the reaction was stirred at room temperature for 18 h. The reaction was diluted with ethyl acetate and washed with saturated bicarbonate and brine. The organic layer was collected, dried over anhydrous sodium sulfate, filtered, and concentrated in vacuo. The crude material was purified via silica gel chromatography (0-100% ethyl acetate:hexanes). Fractions containing desired product were repurified via HPLC to afford pure compound 23 (14.2 mg, 11.8%). LCMS (ESI) m/z=430.87 [M+H]+. H NMR (500 MHz, DMSO-d6) δ 10.24 (s, 1H), 9.70 (s, 1H), 7.98 (d, J=2.0 Hz, 1H), 7.93-7.87 (m, 3H), 7.85 (s, 1H), 7.51 (tdt, J=7.9, 6.8, 3.4 Hz, 3H), 7.42 (dd, J=8.0, 2.0 Hz, 1H), 7.35 (d, J=8.1 Hz, 1H), 7.21-7.15 (m, 2H), 7.08-7.03 (m, 2H), 7.01-6.95 (m, 1H), 3.88 (s, 2H), 2.22 (s, 3H).

Compound 24

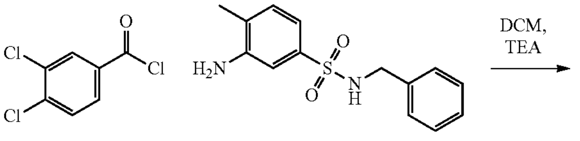

14-1

-continued

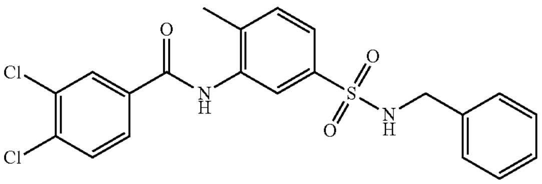

24

3,4-Dichlorobenzoylchloride (24.7 mg, 0.12 mmol) and compound 14-1 (35.0 mg, 0.13 mmol) were combined and suspended in DCM (1 mL). TEA (50.2 μL, 0.36 mmol) was then added and the reaction was stirred at room temperature for 5 h. The reaction was diluted with dichloromethane and washed with water and brine. The organic layer was collected, dried over anhydrous sodium sulfate, filtered, and concentrated in vacuo. The crude material was purified via silica gel chromatography (0-100% ethyl acetate:hexanes) to afford pure compound 24 (21.7 mg, 40.4%). LCMS (ESI) m/z=448.78 [M+H]+. 1H NMR (500 MHz, Chloroform-d) δ 8.25 (s, 1H), 8.12 (d, J=2.0 Hz, 1H), 7.96 (d, J=2.0 Hz, 1H), 7.70 (dd, J=8.4, 2.1 Hz, 1H), 7.55-7.48 (m, 2H), 7.29-7.20 (m, 4H), 7.18 (dd, J=7.7, 1.9 Hz, 2H), 4.07 (s, 2H), 2.33 (s, 3H).

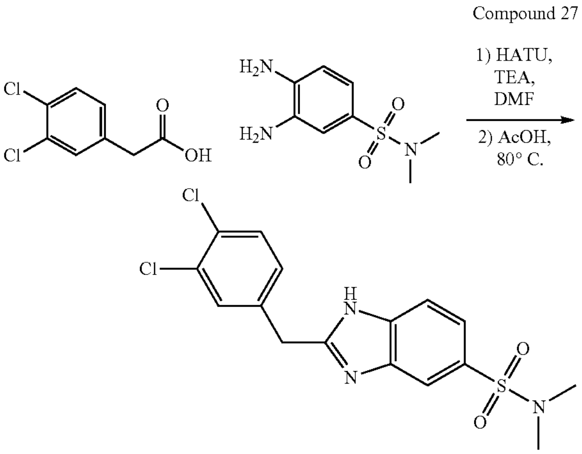

3,4-Dichlorophenylacetic acid (105.4 mg, 0.51 mmol), 3,4-diamino-N,N-dimethylbenzene-1-sulfonamide (103.8 mg, 0.48 mmol) and HATU (277.1 mg, 0.73 mmol) were combined and suspended in DMF (2 mL). TEA (200.7 μL, 1.44 mmol) was then added and the reaction was stirred at room temperature for 5 h. The reaction mixture was concentrated under nitrogen and the crude material was resuspended in acetic acid (3 mL) and the resulting mixture was heated to 80° C. for 4 h. The reaction was quenched with water and basified with saturated sodium bicarbonate. The resulting mixture was extracted with ethyl acetate. The organic layer was collected, dried over anhydrous sodium sulfate, filtered, and concentrated in vacuo. The crude material was purified via silica gel chromatography (0-100% ethyl acetate:hexanes). Fractions containing product were collected and repurified via HPLC to afford pure compound 28 (15.9 mg, 8.6%). LCMS (ESI) m/z=384.17 [M+H]+. $^1$H NMR (500 MHz, Chloroform-d) δ 8.05 (s, 1H), 7.82 (d, J=8.2 Hz, 1H), 7.67 (d, J=8.3 Hz, 1H), 7.61 (s, 1H), 7.39 (d, J=7.0 Hz, 1H), 7.27 (s, 1H), 4.62 (s, 2H), 2.57 (s, 6H).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of formula (I)

(I)

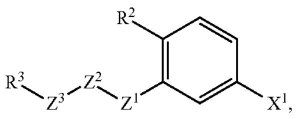

or a pharmaceutically acceptable salt thereof, wherein, independently for each occurrence, $X^1$ is —$S(O)_2R^1$ or —C(═O)$NR^8$($C_{1-3}$ alkyl), wherein $C_{1-3}$ alkyl is optionally substituted with one or more $C_{6-10}$ aryl;

$R^1$ is $C_{1-2}$ alkyl or —$NR^4R^5$;

$R^4$ is H or $C_{1-3}$ alkyl;

$R^5$ is $C_{1-3}$ alkyl or $C_{6-10}$ aryl, or $R^4$ and $R^5$, together with the nitrogen atom to which they are attached, optionally form a $C_{5-8}$ heterocyclyl;

$R^2$ is $C_{1-3}$ alkyl, —$OR^6$, or halogen;

$R^6$ is H, $C_{1-3}$ alkyl, or —C(halogen)$_3$;

$Z^1$ is —C(═O)— or —$NR^8$—;

each $R^8$ is independently H or $C_{1-3}$ alkyl;

$Z^2$ is —C(═O)— or —$NR^8$—, or $R^2$, $Z^2$, and $Z^1$, taken together with the atoms to which they are attached, form a $C_{5-6}$ heteroaryl, $Z^3$ is absent or $C_{1-3}$ alkylene; and $R^3$ is $C_{6-10}$ aryl, $C_{5-6}$ heteroaryl, or $C_{5-8}$ heterocyclyl, wherein $R^3$ is substituted with one or more groups independently selected from $C_{1-3}$ alkyl, $C_{5-8}$ heterocyclyl, —OH, halogen, —NHC(═O)($C_{1-3}$ alkyl), and —NH($C_{1-3}$ alkyl); and wherein each $C_{1-3}$ alkyl, $C_{6-10}$ aryl, $C_{5-6}$ heteroaryl, and $C_{5-8}$ heterocyclyl is independently optionally substituted with one or more groups independently selected from $C_{1-3}$ alkyl, $C_{6-10}$ aryl, $C_{5-8}$ heterocyclyl, halogen, —C(halogen)$_3$, —OH, —$NO_2$, —NHC(═O) ($C_{1-3}$ alkyl), and —NH($C_{1-3}$ alkyl);

provided the compound is not

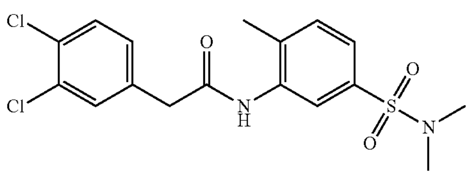

or

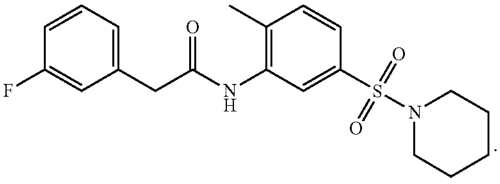

2. The compound of claim 1, wherein the compound is a compound of formula (II)

(II)

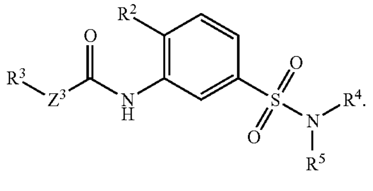

3. The compound of claim 1, wherein $R^4$ is H.

4. The compound of claim 1, wherein $R^4$ is $C_{1-3}$ alkyl.

5. The compound of claim 1, wherein $R^5$ is $C_{1-3}$ alkyl.

6. The compound of claim 1, wherein $R^4$ and $R^5$, together with the nitrogen atom to which they are attached, form a $C_{5-8}$ heterocyclyl.

7. The compound of claim 1, wherein $R^5$ is $C_{1-3}$ alkyl substituted with one or more $C_{6-10}$ aryl.

8. The compound of claim 1, wherein $R^5$ is $C_{6-10}$ aryl optionally substituted with one or more groups independently selected from $C_{1-3}$ alkyl, $C_{6-10}$ aryl, $C_{5-8}$ heterocyclyl, halogen, —C(halogen)$_3$, —OH, —$NO_2$, —NHC(═O)($C_{1-3}$ alkyl), and —NH($C_{1-3}$ alkyl).

9. The compound of claim 1, wherein $R^2$ is $C_{1-3}$ alkyl.

10. The compound of claim 1, wherein $R^2$ is halogen.

11. The compound of claim 1, wherein $Z^3$ is $C_{1-2}$ alkylene.

12. The compound of claim 1, wherein $R^3$ is $C_{6-10}$ aryl, substituted with one or more groups independently selected from $C_{1-3}$ alkyl, $C_{5-8}$ heterocyclyl, —OH, halogen, —NHC(═O)($C_{1-3}$ alkyl), and —NH($C_{1-3}$ alkyl).

13. The compound of claim 12, wherein $R^3$ is substituted with one or more halogen.

14. The compound of claim 1, wherein $R^3$ is

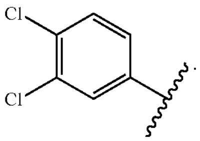 [SMILES: *c1ccc(Cl)c(Cl)c1]

15. The compound of claim 1, wherein the compound is selected from

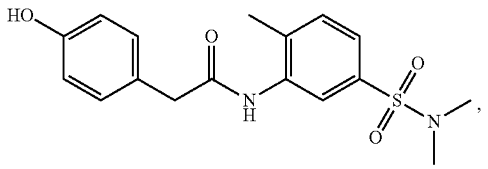
,
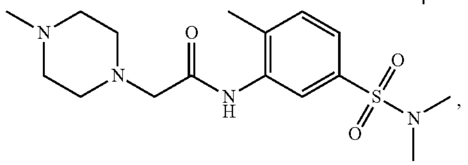
,
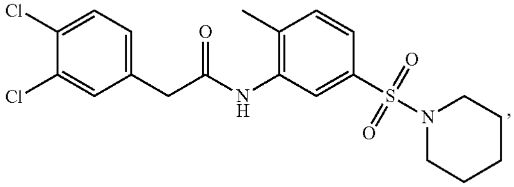
,
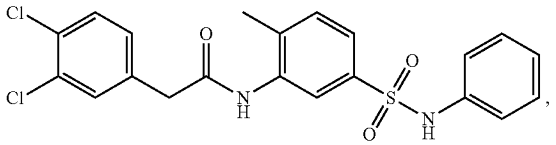
,
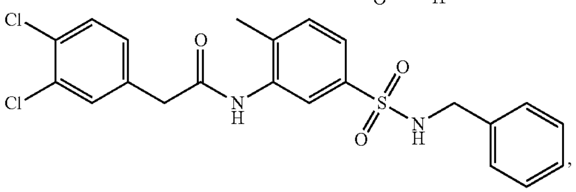
,
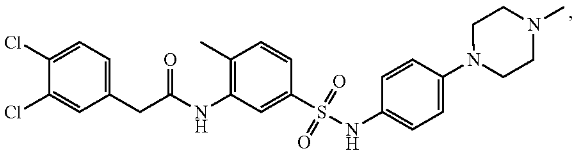
,
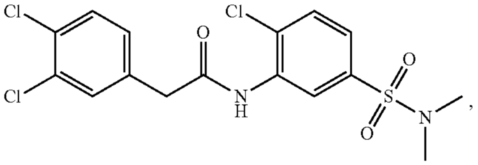
, -continued

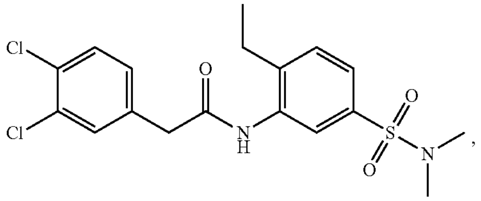
,
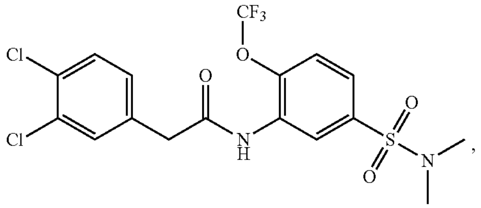
,
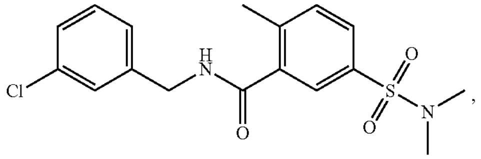
,
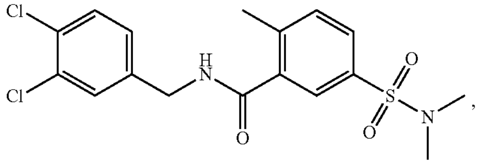
,
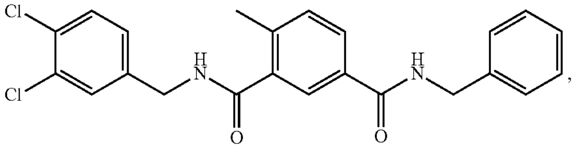
,
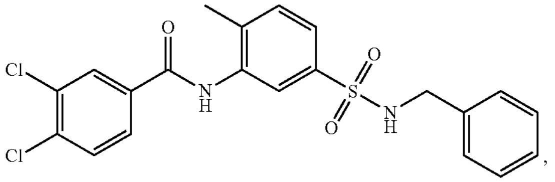
,
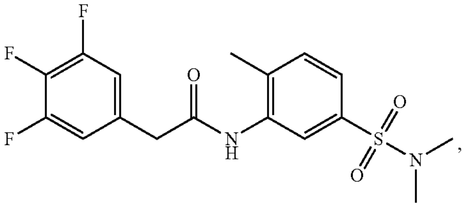
,
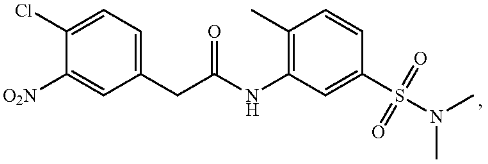
,
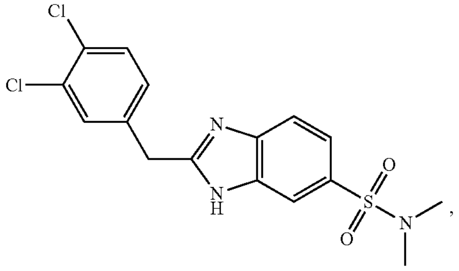
, and -continued

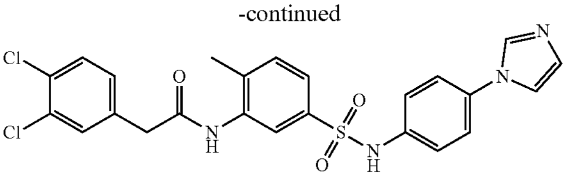, or a pharmaceutically acceptable salt thereof.

16. A pharmaceutical composition comprising a compound of claim 1 and a pharmaceutically acceptable carrier.

17. A method of treating a disease or disorder associated with ubiquitin-specific protease 28 (USP28), comprising administering to a subject in need thereof a compound of claim 1, or a pharmaceutically acceptable salt thereof.

18. The method of claim 17, wherein the disease or disorder associated with USP28 is cancer.

19. A compound, or a pharmaceutically acceptable salt thereof, selected from:

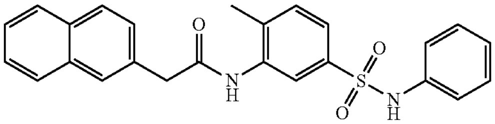 and

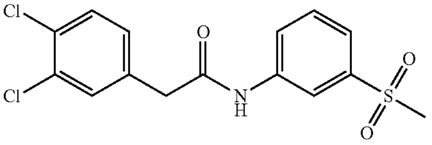.

20. A method of treating a disease or disorder associated with ubiquitin-specific protease 15 (USP28), comprising administering to a subject in need thereof a compound, or a pharmaceutically acceptable salt thereof, selected from:

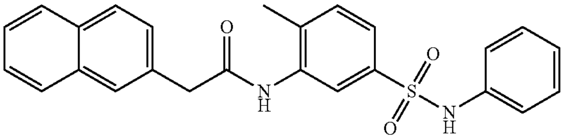,

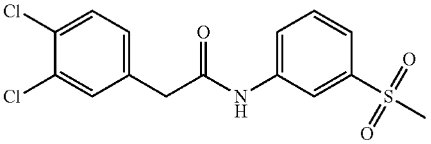,

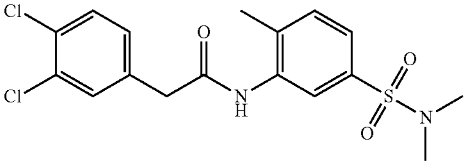,

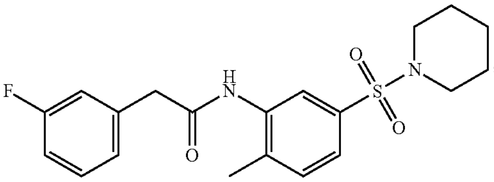, and

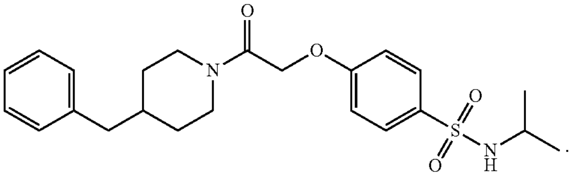.

21. The method of claim 20, wherein the disease or disorder associated with USP28 is cancer.

* * * * *